(12) United States Patent
Zheng et al.

(10) Patent No.: US 8,017,786 B2
(45) Date of Patent: Sep. 13, 2011

(54) SUBSTITUTED β-PHENYL-α-HYDROXY-PROPANOIC ACID, SYNTHESIS METHOD AND USE THEREOF

(75) Inventors: Xiaohui Zheng, Xi'an Shaanxi (CN); Qunzheng Zhang, Xi'an Shaanxi (CN); Shixiang Wang, Xi'an Shaanxi (CN); Xinfeng Zhao, Xi'an Shaanxi (CN)

(73) Assignee: Northwest University (CN)

( * ) Notice: Subject to any disclaimer, the term of this patent is extended or adjusted under 35 U.S.C. 154(b) by 0 days.

(21) Appl. No.: 12/301,069

(22) PCT Filed: May 14, 2007

(86) PCT No.: PCT/CN2007/001550
§ 371 (c)(1), (2), (4) Date: Jan. 27, 2009

(87) PCT Pub. No.: WO2007/131446
PCT Pub. Date: Nov. 22, 2007

(65) Prior Publication Data
US 2009/0131677 A1    May 21, 2009

(30) Foreign Application Priority Data
May 15, 2006 (CN) .......................... 2006 1 0042787

(51) Int. Cl.
C07D 211/78 (2006.01)
(52) U.S. Cl. ......... 546/318; 560/180; 560/184; 560/190
(58) Field of Classification Search ................... 568/319, 568/325, 327
See application file for complete search history.

(56) References Cited

FOREIGN PATENT DOCUMENTS

| CN | 1161140 C | 8/2004 |
|---|---|---|
| CN | 1583710 A | 2/2005 |
| CN | 1868998 | 11/2006 |
| FR | 2842523 A | 1/2004 |
| RU | 2092169 C1 | 10/1997 |
| WO | 03002575 A | 1/2003 |

OTHER PUBLICATIONS

Hcaplus 1964:15870, "alpha-Hydroxy acid amides. A convenient synthesis", Johnson et. al., 1963.*
Hcaplus 1921:15268, "Resolutation of racemic acids by optically active alcohols.II. The resolutation of atrolactinic and alpha-hydroxy-Beta-phenylpropionic acidds by 1-menthol", Wren et. al., 1921.*
Hcaplus 2001:321323, "InCl3-Catalyzed direct aldol reactions of glyoxylic acid monohydrate and gloyoxylates with various ketones: scope and limitations", Loh et. al., 2001.*
Caplus Abstract, "Novel steroid esters useful against skin disorders", Gubernick et. al., 1997.*
Peter I.Dalko, et al., "Stereoselective Hetero-Claisen Rearrangement of Camphor derived Oxazoline-N-oxides", Tetrahedon Letters, 39 (1998) 2107-2110.

Remo Gamboni, et al., "Structure and Diastereoselectivity of the A-Hydroxylation of Chiral Ester Enolates By Molybdenum Peroxo Complex", Tetrahedon Letters, vol. 27, No. 34 (1986) 3999-4002.
Merritt B. Andrus, et al., "Asymmetric Phase-Transfer Catalyzed Glycolate Alkylation, Investigation of the Scope, and Application to the Synthesis of (-)-Ragaglitazar", Journal Org. Chemistry (JOC), vol. 70, No. 23, (2005) 9470-9479.
European Search Report for Application No. 07721123.3 -2103/ 2019090 dated Dec. 30, 2009.
Johnson, et al., "Hydroxy Acid Amides. A Convenient Synthesis," Journal of Organic Chemistry, vol. 28, 1963, pp. 3255-3256.
XP-002559338 retrieved from database accession No. BRN2102386, Aspelund: ACTA Academiae Aboensis, Series B, Mathematica Et Physica, vol. 10, No. 14, 1937, pp. 13-36.
XP-002559339 retrieved from database accession No. BRN1949612, Van Der Stelt et al: Recueil Des Travaux Chimiques Des Pays-Bas, vol. 92, 1973, pp. 493-512.
XP-002559340 retrieved from database accession No. BRN2677217, Morren: Chem. Abstrats, vol. 56, 1962, p. 2329.
XP-002559341 retrieved from database accession No. BRN2387441; Geffken et al: Archive Der Pharmazie, vol. 319, No. 7, 1986, pp. 577-582.
XP-002559342 retrieved from database accession No. BRN3291354; Aspelund: Acta Academiae Aboensis, Series B, Mathematica Et Physica, vol. 11, No. 2, 1937, p. 15.
XP-002559343 retrieved from database accession No. BRN6394184; Gowal, et al: Helvetica Chimica Acta, vol. 68, 1985, pp. 2132-2139.
XP-002559344 retrieved from database accession No. BRN4541943; Ojima et al: Tetrahedron Letters, vol. 21, 1980, pp. 3907-3910.

(Continued)

*Primary Examiner* — Janet Andres
*Assistant Examiner* — Heidi Reese
(74) *Attorney, Agent, or Firm* — Cantor Colburn LLP

(57) ABSTRACT

The present invention relates to a compound of the formula (I), wherein $R_1$, $R_2$ and $R_3$ are each independently selected from H, OH, F, Cl, Br, methoxy and ethoxy; or alternatively, $R_1$ and $R_2$ together form —OCH$_2$O—, $R_3$ is selected from H, OH, methoxy, ethoxy and halogens; $R_4$ is OH or acyloxy; $R_5$ is cycloalkoxyl, amino and substituted amino, and when $R_5$ is selected from amino, at least one of $R_1$, $R_2$ and $R_3$ is not H. The present invention further relates to a process for synthesizing a compound of the formula (I), and use of the compound of the formula (I) in the manufacture of a medicament for the prevention or treatment of cardiovascular or cerebrovascular diseases.

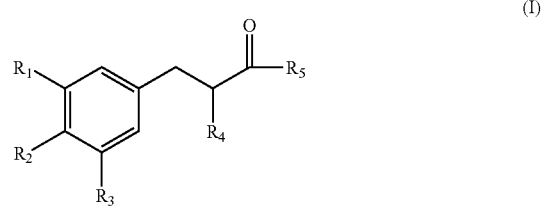

(I)

16 Claims, 4 Drawing Sheets

OTHER PUBLICATIONS

XP-002559345 retrieved from database accession No. BRN4557169; Ojima et al: Tetrahedron Letters, vol. 21, 1980, pp. 3907-3910.

XP-002559346 retrieved from database accession No. BRN5065337; Ojima et al: Chemistry Letters, 1980, pp. 853-856.

XP-002559347 retrieved from database accession No. BRN5130401; Ojima et al: Chemistry Letters, 1980, pp. 853-856.

XP-002559348 retrieved from database accession No. BRN6607392; Wuensch et al: Tetrahedron Asymmetry, vol. 4, No. 11, 1993, pp. 2307-2310.

XP-002559349 retrieved from database accession No. BRN6630225; Harada et al: Tetrahedron Letters, vol. 34, No. 38, 1993, pp. 6091-6094.

XP-002559350 retrieved from database accession No. BRN7242845; Murakami, et al: Tetrahedron Letters, vol. 36, No. 16, 1995, pp. 2785-2788.

XP-002559351 retrieved from database accession No. BRN7294414; Nagatsu et al: Chemical & Pharmaceutical Bulletin, vol. 43, No. 5, 1995, pp. 887-889.

XP-002559352 retrieved from database accession No. BRN7532496; Uchida et al: Journal of Antibiotics, vol. 49, No. 9, pp. 886-889, 1996.

XP-002559353 retrieved from database accession No. BRN 8381662; Ishida et al: Tetrahedron, vol. 55, No. 36, 1999, pp. 10971-10988.

Influence of Borneal to Drug Permeability of BBB and Neuroprotective Mechanism of Borneal Combined with Salvianolic Acid B and Saponins of Panax Notoginseng; Nov. 1, 2007; Retrieved from http://10.1.10.5/kns50/scdbsearch/scdetail.aspx?QueryID=10&CurRec=1.

China Academic Journal Electronic Publishing House, 1994-2011, pp. 362-364.

* cited by examiner

SUBSTITUTED β-PHENYL-α-HYDROXY-PROPANOIC ACID, SYNTHESIS METHOD AND USE THEREOF

TECHNICAL FIELD

The present invention relates to a substituted β-phenyl-α-hydroxyl-propionic acid derivative, a process for synthesizing the same, and use thereof for the manufacture of a medicament for treatment and prevention of cardiovascular and cerebrovascular diseases.

BACKGROUND ART

Dan-shen Root (*Radix Salviae Militiorrhizae*) is a traditional Chinese medicine for treatment of cardiovascular and cerebrovascular diseases with definite therapeutic effects. At present, it is generally presumed that salvianic acid (chemical name: β-(3,4-dihydroxyphenyl)-α-hydroxyl-propionic acid) is the main active ingredient in the water-soluble components of Dan-shen Root. It is demonstrated in Pharmacological tests that β-phenyl-α-hydroxylpropionic acid is the pharmacologically active portion in propanoid acid, but its potency is not desirable. Thus, the substituted β-phenyl-α-hydroxylpropionic acid was modified, and the resulting modified derivatives might possess the same or greater potency than the parent compound, and might also exhibit an improved therapeutic effect in the treatment and prevention of cardiovascular and cerebrovascular diseases. For example, borneol is capable of passing through cardiocerebral barrier, while propanoid acid is not prone to pass through cardiocerebral barrier. Therefore, propanoid acid may be modified in structure by incorporating the chemical structure of borneol.

DISCLOSURE OF THE INVENTION

One object of the present invention is to provide a substituted β-phenyl-α-hydroxy-propionic acid derivative and a process for synthesizing the same, as well as use of the substituted β-phenyl-α-hydroxy-propionic acid derivative in the manufacture of a medicament for prevention and treatment of cardiovascular and cerebrovascular diseases.

In one aspect of the present invention a substituted β-phenyl-α-hydroxy-propionic acid derivative, specifically a compound of the formula (I), is provided:

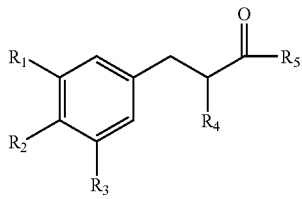
(I)

Wherein, $R_1$, $R_2$, $R_3$ are each independently selected from the group consisting of H, OH, F, Cl, Br, methoxy and ethoxy; or alternatively, $R_1$ and $R_2$ together form —OCH$_2$O—, $R_3$ is selected from the group consisting of H, OH, methoxy, ethoxy and halogens;

$R_4$ is OH or acyloxy;

$R_5$ is selected from the group consisting of cycloalkoxyl, amino and substituted amino, with the proviso that when $R_5$ is amino, then at least one of $R_1$, $R_2$ and $R_3$ is not H.

In one embodiment of the present invention, $R_4$ is OH.

In another embodiment of the present invention, $R_4$ is aroyloxy or heterocyclic radical-substituted acyloxy. Preferably, $R_4$ is o-acetoxybenzoyloxy, 3-pyridinylbenzoyloxy or 4-pyridinylbenzoyloxy.

In a further embodiment of the present invention, $R_5$ is:

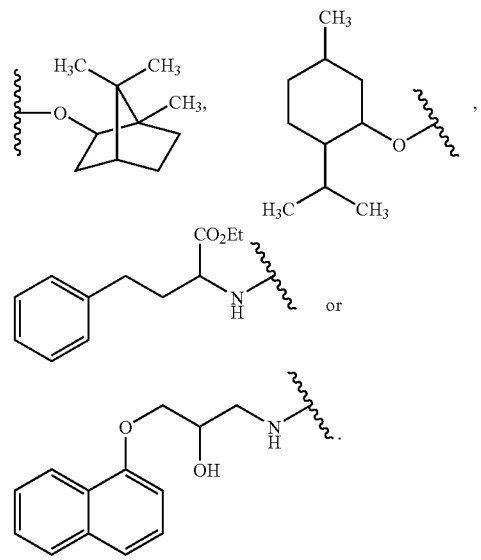

In a still further embodiment, $R_1$ and $R_2$ respectively are OH.

In a still further embodiment, $R_1$ and $R_2$ together form —OCH$_2$O—.

In a preferred embodiment, when $R_1$ and $R_2$ respectively are OH, then $R_3$=H, $R_4$=OH, and

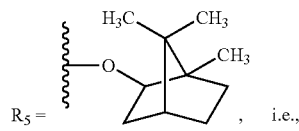

i.e., the compound is bornyl β-(3,4-dihydroxylphenyl)-α-hydroxylpropionate ester as shown in formula (II).

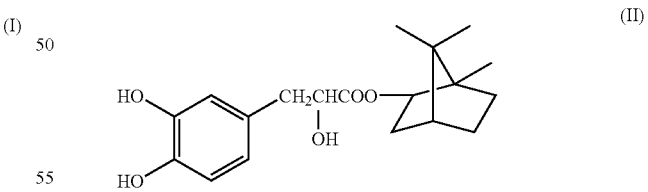
(II)

In another preferred embodiment, when $R_1$ and $R_2$ together form —OCH$_2$O—, then $R_3$=H,

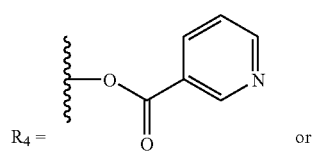

or

-continued

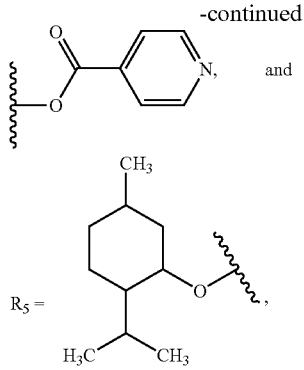

or alternatively, $R_3=H$,

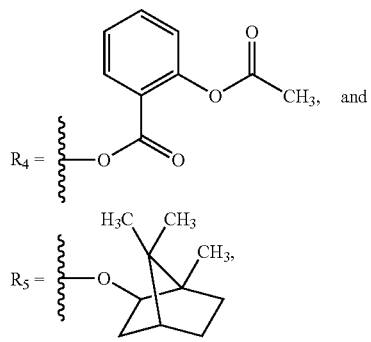

or further alternatively, $R_3=H$, $R_4=OH$, and

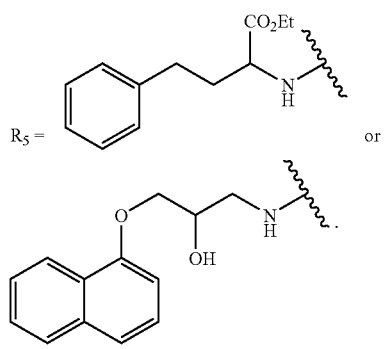

In another aspect of the present invention, a process for synthesizing a compound of the formula (I), is provided, which comprises: reacting a compound of the formula (III) with a compound of formula (IV) or a hydrate thereof in the presence of a catalyst:

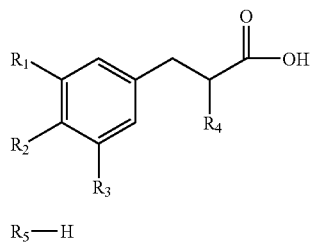

(III)

$R_5$—H    (IV)

Wherein $R_1$, $R_2$, $R_3$, $R_4$ and $R_5$ have the same meanings as defined above for the formula (I);

Or alternatively, said process comprises: reacting a compound of the formula (V) with a compound of the formula (VI) or a hydrate thereof in the present of a catalyst:

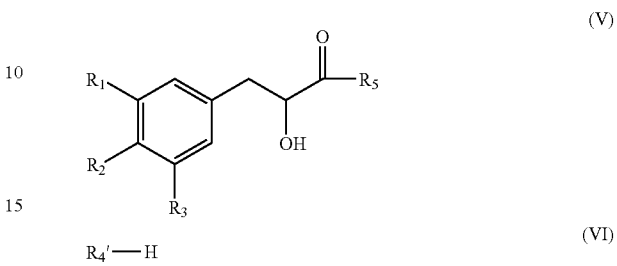

$R_4'$—H    (VI)

Wherein $R_1$, $R_2$, $R_3$ and $R_5$ have the same meanings as defined above for the formula (I), and $R_4'$ is acyloxy.

The said catalyst can be selected from concentrated $H_2SO_4$, silicotungstic acid, phosphomolybdic acid, p-toluene sulfonic acid, $S_2O_8^{2-}/ZrO_2$, aluminum trichloride, zinc chloride and/or magnesium chloride. Preferably, the said catalyst is p-toluene sulfonic acid, $S_2O_8^{2-}/ZrO_2$, aluminum trichloride and/or zinc chloride. It is particularly advantageous to use p-toluene sulfonic acid and/or $S_2O_8^{2-}/ZrO_2$.

The reaction molar ratio of the compound of the formula (III) to the compound of the formula (IV) can be 1:0.8~1:1.5, preferably 1:1~1:1.5, more preferably 1:1.25~1:1.5, most preferably 1:1.5.

The reaction molar ratio of the compound of the formula (V) to the compound of the formula (VI) can be 1:0.8~1:1.5, preferably 1:1~1:1.5, more preferably 1:1.25~1:1.5, most preferably 1:1.5.

Optionally, the reaction is conducted in a solvent. The solvent may be selected from the group consisting of ethyl acetate, dichloromethane, tetrahydrofuran, acetone, toluene, 1,4-dioxane and N,N-dimethylformamide. Preferably, the solvent is selected from the group consisting of tetrahydrofuran, acetone, toluene, 1,4-dioxane, and N,N-dimethylformamide. More preferably, the solvent is selected from tetrahydrofuran and acetone. Most preferably tetrahydrofuran is used as the solvent. These solvents can be used either alone or in any combination.

The reaction temperature can be varied depending on the solvent being used. Advantageously, it is controlled within the range of 0° C.~150° C. Preferably, the reaction temperature is 25° C.~100° C. More preferably, the reaction temperature is 65° C.

The reaction duration can be 2 h~24 h, preferably 5 h~15 h, more preferably 8 h~12 h, most preferably 8 h.

In one specific embodiment, there provided is a process for synthesizing a compound of the formula (II), which comprises: reacting β-(3,4-dihydroxylphenyl)-α-hydroxylpropionic acid with borneol in the presence of a catalyst. The catalyst can be a Lewis acid catalyst, such as toluene sulfonic acid, $S_2O_8^{2-}/ZrO_2$, aluminum trichloride and/or zinc chloride, preferably $S_2O_8^{2-}/ZrO_2$. In the said process, the molar ratio of β-(3,4-dihydroxylphenyl)-α-hydroxylpropionic acid to borneol can be 1:1~1:1.5, preferably 1:1.25~1:1.5, more preferably 1:1.5. The reaction is conducted in a solvent, which can be selected from the group consisting of tetrahydrofuran, toluene, 1,4-dioxane or N,N-dimethylformamide, preferably tetrahydrofuran. The reaction temperature can be varied depending on the solvent being used, and is generally controlled within the range of 65° C.~150° C., preferably at 65° C. The reaction duration can be 8 h~12 h, preferably 8 h.

When $S_2O_8^{2-}/ZrO_2$ is used as the catalyst, the $S_2O_8^{2-}/ZrO_2$ can be optionally prepared by the following process: adding aqueous ammonia to $ZrOCl_2$ solution at 0~10° C. to reach a pH of 9-12, aging, washing the pellets to be free of Cl⁻, heating in an oven to dryness, grinding, then adding into a solution of $(NH_4)_2S_2O_8$ for dipping, filtrating, drying, grinding, and then baking at 500~700° C. for 2-5 h, resulting in $S_2O_8^{2-}/ZrO_2$.

In a further aspect of the present invention, there provided is use of the compound of the present invention in the manufacture of a medicament for the prevention and treatment of cardiovascular and cerebrovascular diseases, especially use of bornyl β-(3,4-dihydroxylphenyl)-α-hydroxylpropionate ester (the compound of the formula (II)) in the manufacture of a medicament for prevention and treatment of cardiovascular and cerebrovascular diseases.

Figure 1:
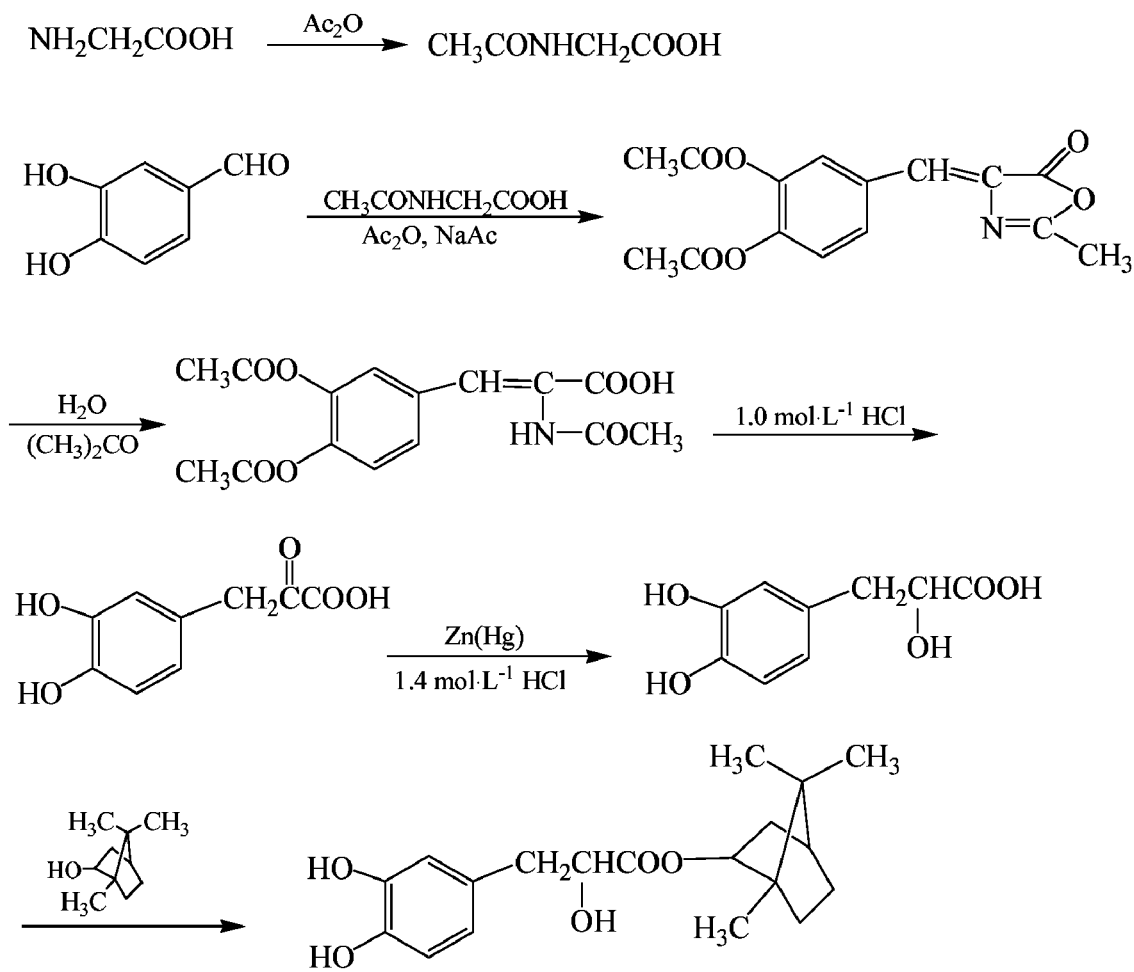
FIG. 1 shows a scheme for the synthesis of the compound of the formula (II) in Example 1, i.e., bornyl β-(3,4-dihydroxylphenyl)-α-hydroxylpropionate ester.

The present invention is further illustrated in conjunction with the following examples on synthesis and the pharmacodynamic tests. However, it should be understood that these examples are merely intended to illustrate, but by no way to limit, the present invention.

EXAMPLE 1

Synthesis (I) of Bornyl β-(3,4-dihydroxylphenyl)-α-hydroxylpropionate Ester (1) Synthesis of Acetyl Glycine Into a 250 mL three-necked flask, 0.33 mol glycine and 100 mL destined water were added and vigorously agitated until dissolution, and 0.67 mol acetic anhydride was slowly added dropwise under stirring. The mixture was vigorously agitated continuously for 50 min, then sucking filtered. The pellets were washed and dried, resulting in a white crystal with a yield of 86.0%.

(2) Synthesis of 2-methyl-4-(3,4-diacetoxybenzylidene)-oxazolone

Into a 250 mL three-necked flask, 0.20 mol 3,4-dihydroxylbenzaldehyde, 0.24 mol acetylglycine and 0.26 mol anhydrous sodium acetate were added, then 189 mL acetic anhydride was added, and mixed homogeneously by stirring. The reaction was performed for 4 h in a 80° C. water bath under stirring, then the temperature was elevated to 100° C. and the reaction was continued for 1 h under stirring. The reaction mixture was cooled to room temperature and then placed in a refrigerator for further cooling. 100 mL water was added to the reaction mixture under stirring to precipitate a yellow crystal at the bottom. After sucking filtration, washing and drying, a yellow crystal was obtained in a yield of 75.0%.

(3) Synthesis of β-(3,4-diacetoxyphenyl)-α-acetamidoacrylic Acid

Into a flask, 0.15 mol 2-methyl-4-(3,4-diacetoxybenzylidene) oxazolone, 166 mL acetone and 166 mL distilled water were added, then slowly heated to boiling, and refluxed by heating for 3 h. The mixture was decolorized using active carbon. After filtration, the filtrate was placed for crystallization, then sucking-filtered, washed and dried resulting in an ecru crystalline powder in a yield of 72.9% was obtained.

(4) Synthesis of β-(3,4-dihydroxylphenyl)pyruvic Acid

Into 0.25 mol β-(3,4-diacetoxyphenyl)-α-acetamidoacrylic acid, 1500 mL of 1 mol·L⁻¹ hydrochloric acid was added. Then the mixture was heated for reflux under stirring for 8 h. After decolorization using active carbon and sucking filtration, the filtrate was concentrated to precipitate as a crystal. The mixture was sucking-filtered, washed and dried, resulting in a white loose crystal in a yield of 48.1%.

(5) Synthesis of β-(3,4-dihydroxylphenyl)-α-hydroxylpropionic Acid

Into 0.17 mol β-(3,4-dihydroxylphenyl)pyruvic acid, 112 g zinc amalgam and 1808 mL of 1.4 mol·L⁻¹ hydrochloric acid solution were added, and the reaction was performed under heating and refluxing for 8 h. After filtration, the filtrate was extracted using ethyl acetate repeatedly, dried using anhydrous $Na_2SO_4$. After removal of ethyl acetate, β-(3,4-dihydroxylphenyl)-α-hydroxylpropionic acid was obtained in a yield of 40.3%.

(6) Synthesis of Bornyl β-(3,4-dihydroxylphenyl)-α-hydroxylpropionate Ester

Into a flask, 0.12 mol β-(3,4-dihydroxylphenyl)-α-hydroxylpropionic acid and 0.18 mol borneol were added, then 0.86 g p-toluene sulfonic acid or 2.00 g of self-made $S_2O_8^{2-}/ZrO_2$ was added as catalyst, and 500 mL tetrahydrofuran was added. The reaction was performed at 65° C. for 8 h. After the completion of the reaction, the catalyst, the solvent and the unreacted borneol were removed to obtain a brown viscous substance, which was further separated using column chromatography to obtain a yellowish oil.

The catalyst $S_2O_8^{2-}/ZrO_2$ was prepared by a process comprising the following steps: preparing a solution of 1 mol·L⁻¹ $ZrOCl_2$ with 0.025 mol $ZrOCl_2·8H_2O$; stirring in an ice-water bath; adding slowly 6 mol·L⁻¹ aqueous ammonia dropwise until pH reached 10; aging for 12 h. suction filtrating; washing the filter cake with distilled water until no Cl⁻ could be determined (using 0.1 mol·L⁻¹ $AgNO_3$ test); baking the filter cake at 110° C. for 10 h; comminuting; soaking in 0.5 mol·L⁻¹ $(NH_4)_2S_2O_8$ solution for 12 h; suction filtrating; drying; comminuting; and baking in a muffle furnace at 600° C. for 3 h to obtain $S_2O_8^{2-}/ZrO_2$.

Figure 2:
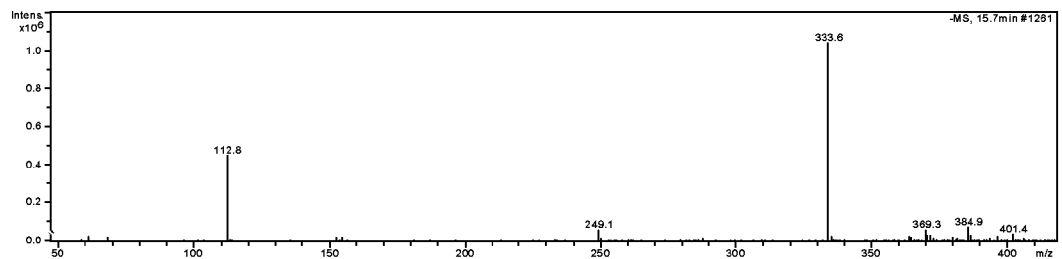
FIG. 2 shows the mass spectrum of the final product obtained in Example 1.
Figure 3:
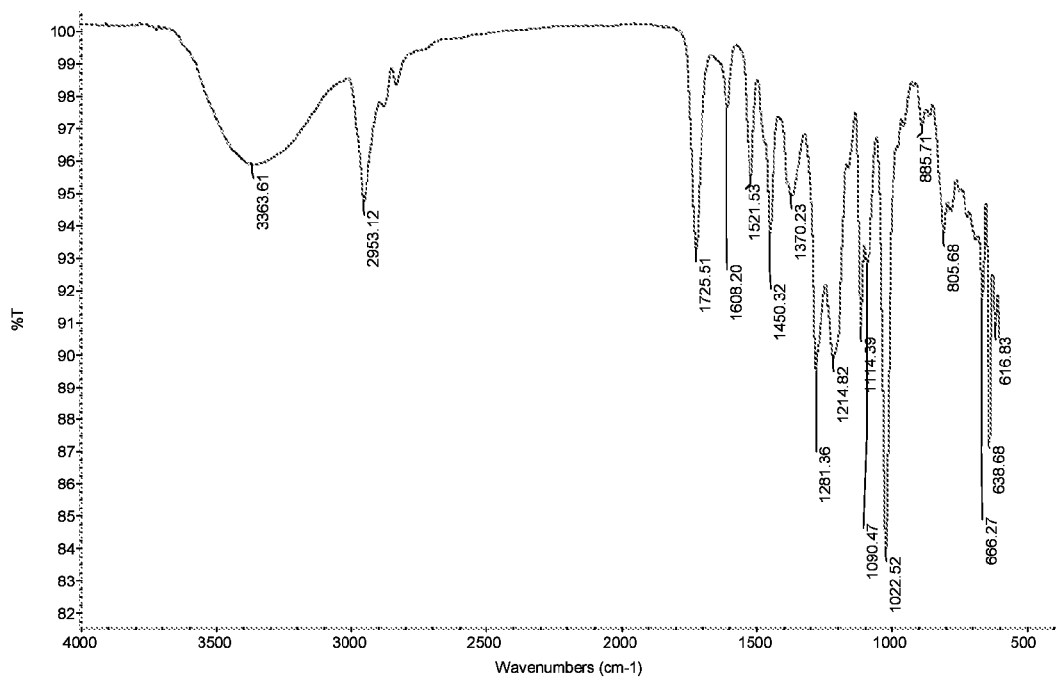
FIG. 3 shows the infrared spectrum of the final product obtained in Example 1.
Figure 4:
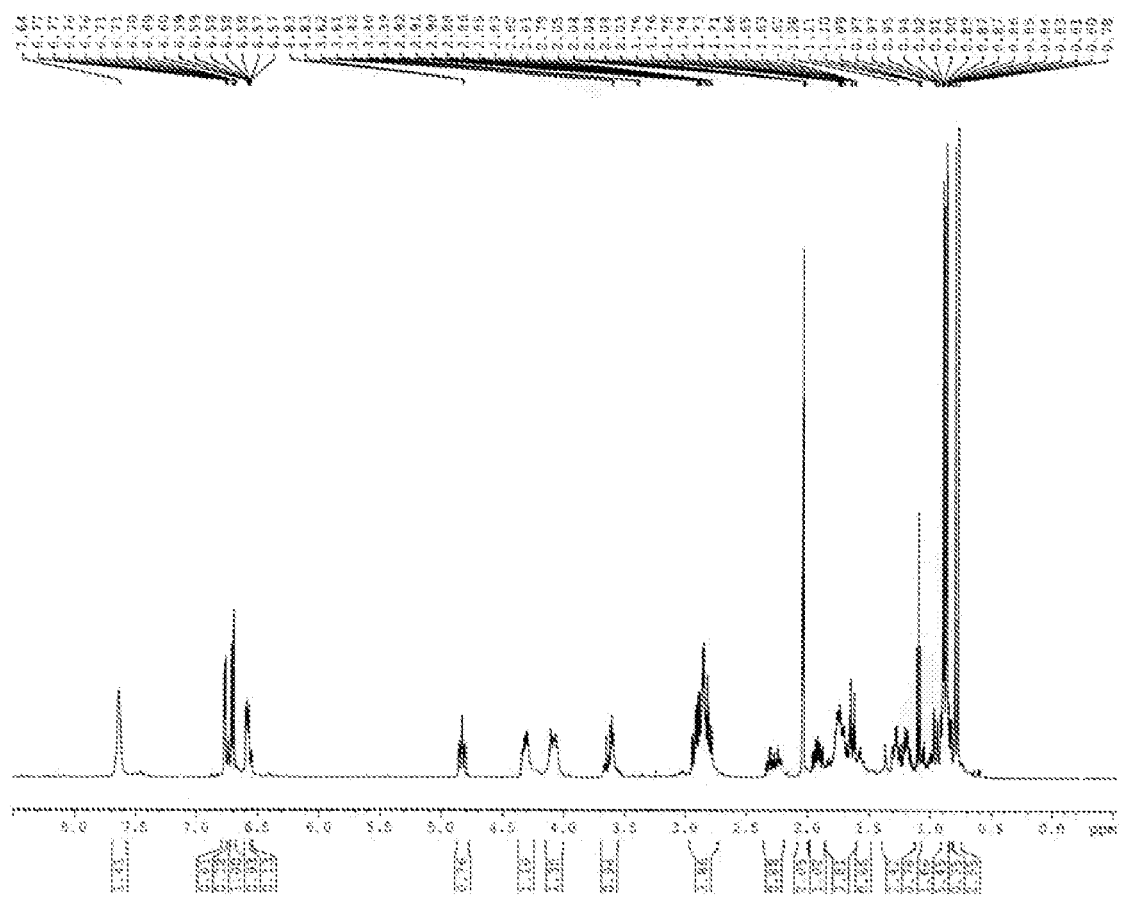
FIG. 4 shows the ¹HNMR spectrum of the final product obtained in Example 1.
Figure 5:
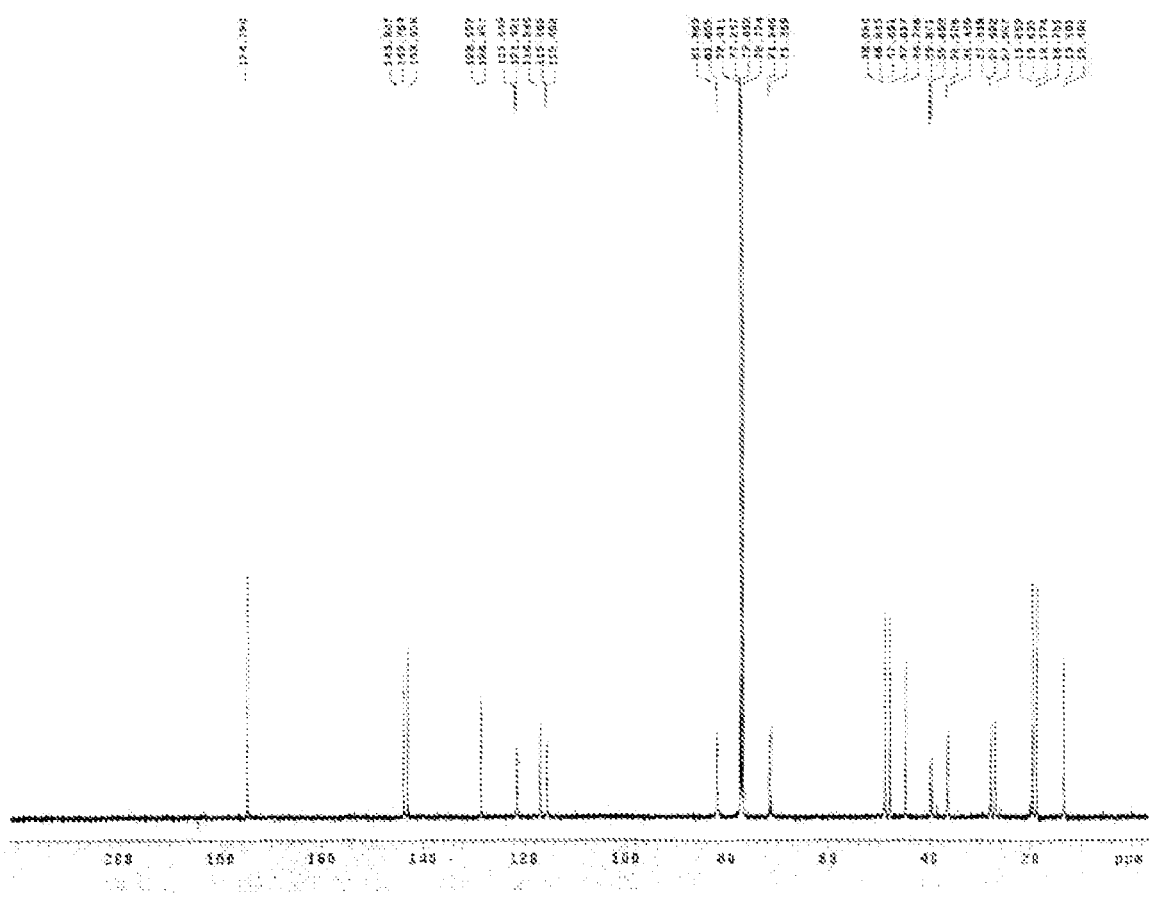
FIG. 5 shows the ¹³CNMR spectrum of the final product obtained in Example 1.

(7) The Mass Spectrum, Infrared Spectrum, ¹HNMR Spectrum and ¹³CNMR Spectrum of the Resulting Yellowish Oil FIG. 2 is the mass spectrum of the obtained yellowish oil, which shows 351.7 is the molecular ion peak of (M+H₂O), and the oil has a molecular weight of 333.69;

FIG. 3 shows the IR (KBr) ν/cm$^{-1}$: 3363.61 (OH), 2953.12 (CH$_3$), 2913.90 (CH$_2$), 1725.51 (C=O), 1608.20, 1521.53, 1450.32 (backbone of the benzene ring), 1281.36 (C=O of the ester), 1114.39 (C—O of the secondary hydroxyl), 885.71 and 805.68 (1,2,4-trisubstituted benzene ring);

FIG. 4 shows the $^1$HNMR (CD$_3$COCD$_3$, 500 MHz) δ: 6.57-7.64 (m, 3H, Ar—H), 4.10-4.32 (m, 1H, —CH(OH)—), 4.83 (t, 1H, —CH—), 2.79-2.92 (m, 2H, —CH$_2$—);

FIG. 5 shows the $^{13}$CNMR (CDCl$_3$, 500 Mz) δ: 174.790, 143.807, 143.056, 128.557, 121.549, 116.895, 115.488, 81.983, 71.646, 48.860, 47.881, 44.798, 39.871, 36.506, 27.918, 27.057, 19.653, 18.774, 13.501.

The above characterization data proved that bornyl β-(3,4-dihydroxylphenyl)-α-hydroxylpropionate ester was obtained by synthesis.

EXAMPLE 2

Synthesis (II) of Bornyl β-(3,4-dihydroxylphenyl)-α-hydroxylpropionate Ester

The synthesis was performed through the same procedure of Example 1, except that 0.12 mol β-(3,4-dihydroxylphenyl)-α-hydroxylpropionic acid and 0.15 mol borneol were added to the three-necked flask, then 0.86 g p-toluene sulfonic acid as catalyst and 500 mL tetrahydrofuran were added, and the reaction was performed at 65° C. for 12 h. After the completion of the reaction, the reaction solvent was removed by vacuum distillation, and the resulting viscous substance was treated by vacuum (1.3×10$^{-3}$ Pa) using an oil pump in a boiling-water bath to remove borneol, then 200 mL ethyl acetate was added. The resulting solution was washed with saturated NaHCO$_3$ solution to remove unreacted β-(3,4-dihydroxylphenyl)-α-hydroxylpropionic acid and p-toluene sulfonic acid. The obtained ethyl acetate layer was concentrated under reduced pressure, resulting in a brown viscous substance, which was further separated by column chromatography, obtaining a yellowish oil. The resultant yellowish oil has the same mass spectrum and infrared spectrum as that in Example 1.

EXAMPLE 3

Synthesis (III) of Bornyl β-(3,4-dihydroxylphenyl)-α-hydroxylpropionate Ester

The synthesis was performed through the same procedure of Example 1, except that 0.1 mol β-(3,4-dihydroxylphenyl)-α-hydroxylpropionic acid and 0.12 mol borneol were added to the three-necked flask, then 1.33 g S$_2$O$_8^{2-}$/ZrO$_2$ as catalyst and 400 mL 1,4-dioxane were added, and the reaction was performed at 100° C. for 8 h. After the completion of the reaction, the catalyst S$_2$O$_8^{2-}$/ZrO$_2$ was removed by sucking filtration, and the solvent was removed by vacuum distillation, and the resulting viscous substance was treated by vacuum (1.3×10$^{-3}$ Pa) using an oil pump in a boiling-water bath to remove borneol. The resultant black brown viscous substance was separated using column chromatography, obtaining a yellowish oil, which has the same mass spectrum and infrared spectrum as that in Example 1.

EXAMPLE 4

Synthesis (IV) of Bornyl β-(3,4-dihydroxylphenyl)-α-hydroxylpropionate Ester

The synthesis was performed through the same procedure of Example 1, except that 0.06 mol β-(3,4-dihydroxylphenyl)-α-hydroxylpropionic acid and 0.09 mol borneol were added to the three-necked flask, then 0.60 g aluminum trichloride as catalyst and 200 mL N,N-dimethylformamide as solvent were added, and the reaction was performed at 150° C. for 10 h. After the completion of the reaction, the solvent was removed by vacuum distillation, and the resulting viscous substance was treated by vacuum (1.3×10$^{-3}$ Pa) using an oil pump in a boiling-water bath to remove borneol. The resultant black brown substance was separated using column chromatography, obtaining a yellowish oil, which has the same mass spectrum and infrared spectrum as that of Example 1.

EXAMPLE 5

Synthesis of Bornyl β-(4-chlorophenyl)-α-hydroxylpropionate Ester (1) 2-methyl-4-(4-chlorobenzylidene)oxazolone was synthesized in a way similar to Example 1 (2), except that 4-chlorobenzaldehyde was used instead of 3,4-dihydroxylbenzaldehyde. A brown crystal was obtained in a yield of 87.4%.

(2) Synthesis of β-(4-chlorophenyl)-α-acetamidoacrylic Acid 0.10 mol 2-methyl-4-(4-chlorobenzylidene)oxazolone, 110 mL acetone, 110 mL water and 2 mL concentrated hydrochloric acid were added to a flask, heated slowly to boil, and then kept on heating for reflux for 3 h. After decolorization using active carbon and filtration, the filtrate was placed for crystallization, and an orange crystalline powder was obtained in a yield of 81.1% by sucking filtration, washing and drying.

(3) Synthesis of β-(4-chlorophenyl)pyruvic Acid 4.55 g β-(4-chlorophenyl)-α-acetamidoacrylic acid, 91 mL of 1 mol·L$^{-1}$ hydrochloric acid solution and 45 mL THF were added to a flask, and the mixture was heated for reflux for 10 h. After decolorization using active carbon and filtration, the filtrate was placed for crystallization, and an off-white crystalline powder was obtained in a yield of 77.3% by sucking filtration, washing and drying.

(4) Synthesis of β-(4-chlorophenyl)-α-hydroxylpropionic Acid

Into 15.00 g β-(4-chlorophenyl)pyruvic acid, 98.00 g Zn(Hg), 219 mL of 2.5 mol·L$^1$ hydrochloric acid and 35 mL THF solution were added, heated for refluxed for 10 h. After the filtration was performed when the reaction mixture was hot, the filtrate was concentrated to reach 80 mL and stood overnight. After sucking filtration, washing, drying and recrystallizing in boiling-water, a white floccular crystal was obtained in a yield of 64.0%.

(5) Synthesis of Bornyl β-(4-chlorophenyl)-α-hydroxylpropionate Ester

Into a three-necked flask, 0.12 mol β-(4-chlorophenyl)-α-hydroxylpropionic acid and 0.15 mol borneol were added, then 0.86 g p-toluene sulfonic acid as catalyst and 500 mL tetrahydrofuran were added, and the reaction was performed at 65° C. for 12 h. After the completion of the reaction, the reaction solvent was removed by vacuum distillation, the obtained viscous substance was treated by vacuum (1.3×10$^{-3}$ Pa) using an oil pump in a boiling-water bath to remove borneol, then 200 mL ethyl acetate was added to obtain a solution. The resulting solution was washed with saturated NaHCO$_3$ solution to remove unreacted β-(4-chlorophenyl)-α-hydroxylpropionic acid and p-toluene sulfonic acid. The obtained organic phase was concentrated under vacuum, resulting in a brown viscous substance, which was separated using column chromatography to obtain a yellowish oil.

IR (KBr) v/cm$^{-1}$: 3461.45 (OH), 2981.99 (CH$_3$), 2935.46 (CH$_2$), 1731.08 (C=O), 1598.03, 1492.10, 1453.90 (backbone of benzene ring), 1269.86 (C=O of the ester), 1106.22 (C—O of secondary hydroxyl), 846.84 (para-disubstituted);

$^1$HNMR (500 MHz, CDCl$_3$) δ: 6.57-7.64 (m, 3H, Ar—H), 4.10-4.32 (m, 1H, —CH(OH)—), 4.83 (t, 1H, —CH—), 2.79-2.92 (m, 2H, —CH$_2$—), 1.205 (t, 3H, —CH$_3$);

$^{13}$CNMR (500 MHz, CDCl$_3$) δ: 13.5, 19.5, 19.5, 23.3, 30.2, 32.5, 40.8, 45.4, 49.4, 50.6, 71.3, 82.4, 128.7, 128.7, 129.1, 129.1, 131.5, 137.5, 170.8.

EXAMPLE 6

Synthesis of Bornyl β-(3-methoxy-4-hydroxylphenyl)-α-hydroxylpropionate Ester (1) 2-methyl-4-(3-methoxy-4-acetoxybenzylidene)oxazolone was synthesized in a way similar to Example 1 (2), except that 3-methoxy-4-hydroxylbenzaldehyde was used instead of 3,4-dihydroxylbenzaldehyde. A yellow crystal was obtain in a yield of 73.5%.

(2) β-(3-methoxy-4-acetoxyphenyl)-α-acetamidoacrylic acid was synthesized in a way similar to Example 1 (3), except that 2-methyl-4-(3-methoxy-4-acetoxybenzylidene) oxazolone was used instead of 2-methyl-4-(3,4-diacetoxybenzylidene)oxazolone. A ecru loose crystal powder was obtain in a yield of 71.6%.

(3) β-(3-methoxy-4-hydroxylphenyl)pyruvic acid was synthesized in a way similar to Example 1 (4), except that β-(3-methoxy-4-acetoxyphenyl)-α-acetamidoacrylic acid was used instead of β-(3,4-diacetoxyphenyl)-α-acetamidoacrylic acid. A yellowish loose crystal powder was obtained in a yield of 64.2%.

(4) β-(3-methoxy-4-hydroxylphenyl)-α-hydroxylpropionic acid was synthesized in a way similar to Example 5 (4), except that β-(3-methoxy-4-hydroxylphenyl)pyruvic acid was used instead of β-(3,4-dihydroxylphenyl)pyruvic acid. A yellowish oil or crystal was obtained in a yield of 77.8%.

(5) Bornyl β-(3-methoxy-4-hydroxylphenyl)-α-hydroxylpropionate ester was synthesized in a way similar to Example 5 (5), except that β-(3-methoxy-4-hydroxylphenyl)-α-hydroxylpropionic acid was used instead of β-(3,4-dihydroxylphenyl)-α-hydroxylpropionic acid. A yellowish crystal was obtained in a yield of 59.8%.

IR (KBr) v/cm$^{-1}$: 3363.61 (OH), 2953.12 (CH$_3$), 2913.90 (CH$_2$), 1725.51 (C=O), 1608.20, 1521.53, 1450.32 (backbone of benzene ring), 1281.36 (C=O of the ester), 1114.39 (C—O of the secondary hydroxyl), 885.71, 805.68 (1,2,4-trisubstituted benzene ring), 1237.58, 1027.61 (aryl alkyl ether);

$^1$HNMR (400 MHz, CD$_3$COCD$_3$) δ: 6.679-6.869 (m, 3H, Ar—H), 4.920-4.983 (m, 1H, —CH—), 4.257-4.286 (t, 1H, —CH(OH)—), 3.819 (s, 3H, —OCH$_3$), 2.804-2.978 (m, 2H, —CH$_2$—);

$^{13}$CNMR (500 MHz, CD$_3$COCD$_3$) δ: 13.5, 19.5, 19.5, 23.3, 30.2, 32.5, 41.1, 45.4, 49.4, 50.6, 56.1, 71.3, 82.4, 113.1, 116.8, 121.4, 133.0, 142.9, 151.3, 170.8.

EXAMPLE 7

Synthesis of Menthyl β-(benzo[1,3]dioxol-5-yl)-α-(nicotinoyloxy)propionate Ester (1) 2-methyl-4-(benzo[1,3]dioxol-5-ylmethylene)-oxazolone was synthesized in a way similar to Example 1 (2), except that benzo[1,3]dioxole-5-carbaldehyde was used instead of 3,4-dihydroxylbenzaldehyde. A yellow crystal was obtained in a yield of 76.5%.

(2) β-(benzo[1,3]dioxol-5-yl)-α-acetamidoacrylic acid was synthesized in a way similar to Example 1 (3), except that 2-methyl-4-(benzo[1,3]dioxol-5-ylmethylene)-oxazolone was used instead of 2-methyl-4-(3,4-diacetoxybenzylidene) oxazolone. An ecru loose crystal powder was obtained in a yield of 78.7%.

(3) β-(benzo[1,3]dioxol-5-yl)pyruvic acid was synthesized in a way similar to Example 1 (4), except that β-(benzo[1,3]dioxol-5-yl)-α-acetamidoacrylic acid was used instead of β-(benzo[1,3]dioxol-5-yl)-α-acetamidoacrylic acid. A yellowish loose crystal was obtained in a yield of 65.4%.

(4) β-(benzo[1,3]dioxol-5-yl)-α-hydroxylpropionic acid was synthesized in a way similar to Example 5 (4), except that β-(benzo[1,3]dioxol-5-yl)pyruvic acid was used instead of β-(3,4-dihydroxylphenyl)pyruvic acid. A yellowish oil or crystal was obtained in a yield of 78.7%.

(5) Menthyl β-(benzo[1,3]dioxol-5-yl)-α-hydroxylpropionate ester was synthesized in a way similar to Example 5 (5), except that β-(benzo[1,3]dioxol-5-yl)-α-hydroxylpropionic acid was used instead of β-(3,4-dihydroxylphenyl)-α-hydroxylpropionic acid. A yellowish oil was obtained.

(6) Synthesis of Menthyl β-(benzo[1,3]dioxol-5-yl)-α-(nicotinoyloxy)propionate Ester Into a three-necked flask, 0.12 mol menthyl β-(benzo[1,3]dioxol-5-yl)-α-hydroxylpropionate ester was dissolved in 15 mL acetone, then an amount of the catalyst DCC/DMAP was added. A solution of 0.15 mol nicotinic acid dissolved in 5 mL acetone was added dropwise in an ice bath. The reaction was performed in the ice bath for 2 h, then under room temperature for 1 h. After the completion of the reaction, vacuum suction filtration was performed, the reaction solvent was removed by distillation, and 200 mL ethyl acetate was added to the resultant viscous substance. The obtained solution was washed with a saturated NaHCO$_3$ solution to remove unreacted nicotinic acid and the catalyst. The organic phase was concentrated under vacuum to obtain a brown viscous substance, which was separated using column chromatography to obtain a yellowish oil, menthyl β-(benzo[1,3]dioxol-5-yl)-α-(nicotinoyloxy)propionate ester in a yield of 45.5%.

IR (KBr) v/cm$^{-1}$: 3056.56 (H—C=C), 2967.42 (CH$_3$), 2940.54 (CH$_2$), 1723.02 (C=O), 1597.32, 1520.17, 1462.10 (backbone of benzene ring), 1452.62, 1480.34, 1585 (backbone of pyridine ring), 1268.53 (C=O of ester), 1235.79, 1017.23 (aryl alkyl ether), 1125.33 (C—O of secondary hydroxyl), 884.43 and 798.62 (1,2,4-trisubstituted);

$^1$HNMR (400 MHz, CD$_3$COCD$_3$.) δ: 7.56-9.00 (m, 4H, Pyridinio-H), 6.679-6.869 (m, 3H, Ar—H), 6.06 (s, 2H, —OCH$_2$O—), 5.10 (m, 1H, —CH(O)—), 4.920-4.983 (m, 1H, —OCH(clcy)-), 2.804-2.978 (m, 2H, —CH$_2$—);

13CNMR (500 MHz, $CD_3COCD_3$) δ: 20.7, 21.0, 21.0, 22.3, 25.7, 28.5, 33.9, 37.8, 39.6, 47.1, 72.6, 75.6, 101.2, 112.7, 115.2, 121.0, 122.1, 126.0, 132.7, 136.4, 146.0, 148.7, 150.4, 151.4, 165.9, 170.8.

EXAMPLE 8

Synthesis of Menthyl β-(benzo[1,3]dioxol-5-yl)-α-(isonicotinoyloxy)propionate Ester The synthesis was performed in a way similar to Example 7, except that isonicotinic acid was used instead of nicotinic acid. A final product of yellowish oil was obtained, in a yield of 47.83%, which was menthyl β-(benzo[1,3]dioxol-5-yl)-α-(isonicotinoyloxy)propionate ester.

IR (KBr) v/cm$^{-1}$: 2966.27 ($CH_3$), 2943.14 ($CH_2$), 1720.82 (C=O), 1592.37, 1517.09, 1467.10 (backbone of benzene ring), 1452.24, 1484.56, 1598.23 (backbone of pyridine ring), 1267.67 (C=O of ester), 1237.58, 1027.61 (aryl alkyl ether), 1103.14 (C—O of secondary hydroxyl), 880.43 and 795.81 (1,2,4-trisubstituted);

$^1$HNMR (400 MHz, $CD_3COCD_3$) δ: 7.56-9.00 (m, 4H, Pyridinio-H), 6.679-6.869 (m, 3H, Ar—H), 6.06 (s, 2H, —$OCH_2O$—), 5.10 (m, 1H, —CH(O)—), 4.920-4.983 (m, 1H, —OCH(clcy)-), 2.804-2.978 (m, 2H, —$CH_2$—);

$^{13}$CNMR (500 MHz, $CD_3COCD_3$) δ: 20.7, 21.0, 21.0, 22.3, 25.7, 28.5, 33.9, 37.8, 39.6, 47.1, 72.6, 75.6, 101.2, 112.7, 115.2, 122.9, 122.9, 126.0, 132.7, 136.4, 146.0, 148.7, 150.3, 150.3, 165.9, 170.8.

EXAMPLE 9

Synthesis of Bornyl β-(benzo[1,3]-dioxol-5-yl)-α-(2-acetoxybenzoyloxy)propionate Ester The steps (1) to (4) of the synthesis were identical to the steps (1) to (4) in example 7.

(5) Bornyl β-(benzo[1,3]-dioxol-5-yl)-α-hydroxylpropionate ester was synthesized in a way similar to Example 5 (5), except that borneol was used instead of menthol, and a yellowish oil was obtained.

(6) Bornyl β-(benzo[1,3]-dioxol-5-yl)-α-(2-acetoxy-benzoyloxy)propionate ester was synthesized in a way similar to Example 7 (6), except that 2-acetoxybenzoic acid was used instead of nicotinic acid, and bornyl β-(benzo[1,3]-dioxol-5-yl)-α-hydroxylpropionate ester was used instead of menthyl β-(benzo[1,3]-dioxol-5-yl)-α-hydroxylpropionte ester. A light brown-yellow oil or crystal was obtained in a yield of 43.8%.

IR (KBr) v/cm$^{-1}$: 2981.99 ($CH_3$), 2935.46 ($CH_2$), 1731.08 (C=O), 1598.03, 1492.10, 1453.90 (backbone of benzene ring), 1269.86 (C=O of ester), 1106.22 (C—O of secondary hydroxyl), 880.43 and 795.81 (1,2,4-trisubstituted), 746.84 (ortho-disubstituted);

$^1$HNMR (400 MHz, $CD_3COCD_3$) δ: 7.18-8.00 (m, 4H, Ar—H), 6.679-6.869 (m, 3H, Ar—H), 6.06 (s, 2H, —$OCH_2O$—), 5.10 (m, 1H, —CH(O)—), 4.920-4.983 (m, 1H, —OCH(clcy)-), 2.804-2.978 (m, 2H, —$CH_2$—);

$^{13}$CNMR (500 MHz, $CD_3COCD_3$) δ: 13.5, 19.5, 19.5, 20.3, 23.3, 30.2, 32.5, 37.8, 45.4, 49.4, 50.6, 56.1, 72.6, 82.1, 112.7, 115.2, 120.9, 121.0, 121.5, 125.5, 130.3, 132.7, 133.5, 146.0, 148.7, 153.6, 165.9, 169.0, 170.8.

EXAMPLE 10

Synthesis of β-(benzo[1,3]-dioxol-5-yl)-α-hydroxyl-N-(3-phenyl-1-ethoxycarbonyl-propyl)propionamide The steps (1) to (4) of the synthesis were identical to the steps (1) to (4) in example 7.

(5) Synthesis of Ethyl 2-amino-4-phenylbutyrate Ester

Into 16.50 g homephenylalanine, 350 mL anhydrous ethanol was added, and dry HCl gas was fed under stirring. The feeding was stopped after 1.5 hr, and the reaction apparatus was changed. The reaction mixture was heated for reflux for 1.5 h. After the completion of the reaction, most of ethanol was removed by distillation to precipitate a large amount of white crystal, and then 19.2 g of white needle crystal was obtained after sucking filtration, washing and drying. The white crystal was dissolved in an aqueous solution, and the PH of the resultant solution was adjusted using a NaOH solution. The solution was extracted using ethyl ether. Then the solvent was removed, resulting in 14.92 g colorless or yellowish liquid in a yield of 78.2%.

(6) Synthesis of β-(benzo[1,3]-dioxol-5-yl)-α-hydroxyl-N-(3-phenyl-1-ethoxycarbonyl-propyl)propionamide Into a flask, 0.40 g β-(benzo[1,3]-dioxol-5-yl)-α-hydroxylpropionic acid and 12 mL $CH_3CN$ were added, and the flask was cooled exteriorly with a mixture of ice and water. 0.62 g ethyl 2-amino-4-phenylbutyrate ester and 0.02 g DMAP were added under agitation generated by a magnetic stirring bar. After the mixture was stirred to clarification, 0.45 g DCC was added. The reaction temperature was elevated naturally to room temperature under stirring, and the reaction was performed at room temperature for 5 h. After the solvent was removed by vacuum distillation, ethyl acetate was added. The obtained solution in ethyl acetate was washed with $NaHCO_3$ solution, aqueous HCl solution, and water, then distilled under vacuum to obtain a crude product of the desired compound. After purification of the crude product by chromatography, 0.39 g white solid was obtained in a yield of 51.3%.

IR (KBr) v/cm$^{-1}$: 3417.26 (alcohol hydroxyl), 3255.79 (NH), 2967.53 ($CH_3$), 2934.21 ($CH_2$), 1723.79 (C=O), 1669.97 (C=O of amide), 1593.37, 1515.19, 1463.13 (backbone of benzene ring), 1239.98, 1026.76 (aryl alkyl ether), 1111.35 (C—O of secondary hydroxyl), 884.45 and 792.17 (1,2,4-trisubstituted); 698.69, 750.62 (monosubstituted benzene ring);

$^1$ HNMR (400 MHz, $CD_3COCD_3$) δ: 6.18-7.50 (m, 8H, Ar—H), 6.13 (s, 2H, —$OCH_2O$—), 4.82 (m, 1H, —CH(NH)—), 4.55 (m, 1H, —CH(OH)—), 4.12 (q, 2H, —$OCH_2$—), 2.804-2.978 (m, 2H, -Ph$CH_2$—), 2.30-2.54 (m, 4H, —$CH_2CH_2$—), 1.31 (t, 3H, —$CH_3$);

$^{13}$CNMR (500 MHz, $CD_3COCD_3$) δ: 14.1, 30.3, 32.3, 41.7, 52.7, 61.3, 73.3, 101.2, 112.7, 115.2, 121.0, 126.1, 128.1, 128.1, 128.9, 128.9, 132.7, 138.0, 146.0, 148.7, 171.5, 172.7.

EXAMPLE 11

Synthesis of 2-hydroxyl-3-(benzo[1,3]-dioxol-5-yl)-N-[2-hydroxyl-3-(1-naphthoxy)-propyl]-propionamide The steps (1) to (4) of the synthesis were identical to the steps (1) to (4) in example 7.

(5) Synthesis of 1-naphthyl Epoxypropyl Ether

Into a 500 mL three-necked round bottom flask, 10.03 g 1-naphthol, 3.1 g NaOH, 20.4 g epichlorohydrin (SIR) and 0.5 g KI were added, then 330 mL ethanol was added. The flask was then placed in a microwave reactor. The reaction was performed at 30° C. under stirring and 300 W microwave irradiation for 12 min. The reaction mixture was then removed and suction filtrated, and the filtrate was concentrated to obtain an oily substance. $H_2O$ was added to the oily substance, and the mixture was extracted with ethyl ether. The ethyl ether layers were combined and washed with a solution of NaOH, then washed with $H_2O$ once. The ether layer was dried using anhydrous magnesium sulfate and concentrated to obtain 12.95 g of the product in a yield of 93.2%.

(6) Synthesis of 1-amino-3-(1-naphthoxy)-2-propanol 450 mL concentrated aqueous ammonia was placed in a reaction flask special for microwave, then 3.0 g 1-naphthyl epoxypropyl ether was added, and the reaction was performed at 40° C. under magnetic stirring and 300 W microwave irradiation for 14 min. After the completion of the reaction, the reaction mixture was concentrated to dryness, then ethyl acetate was added, and the pH was adjusted to acidic with concentrated hydrochloride. After sucking filtration, 1-amino-3-(1-naphthoxy)-2-propanol hydrochloride was obtained, and then dried to result in a white solid. The solid was dissolved in water by heating, and the pH was adjusted to alkaline. After cooling, a large amount of white solid was precipitated out. The precipitate was sucking filtrated and dried, resulting in 2.0 g white solid in a yield of 63%.

(7) Preparation of 2-hydroxyl-3-(benzo[1,3]-dioxol-5-yl)-N-[2-hydroxyl-3-(1-naphthoxy)propyl]-propionamide 0.43 g 1-amino-3-(1-naphthoxy)-2-propanol was dissolved in 15 mL acetone then, 0.45 g DCC and 0.10 g DMAP were added, and 0.40 g β-(benzo[1,3]-dioxol-5-yl)-α-hydroxylpropionic acid dissolved in 5 mL acetone was added dropwise under magnetic stirring. The reaction was performed at room temperature for 1 h, and a large amount of white solid was produced. After the completion of the reaction, the reaction mixture was suction filtrated, and the filtrate was concentrated to dry, then ethyl acetate was added to the resultant dry product and washed with $NaHCO_3$ solution. The ester layer was concentrated to dry, thereby obtaining a brown oily substance, which was purified via preparative liquid chromatography. 0.27 g yellowish oil was obtained in a yield of 32.8%.

IR (KBr) $v/cm^{-1}$: 3409.82 (alcohol hydroxyl), 3251.72 (NH), 2969.37 ($CH_3$), 2944.74 ($CH_2$), 1723.49 (C=O), 1664.74 (C=O of ester), 1591.77, 1519.90, 1469.21 (backbone of benzene ring), 1235.78, 1029.63 (aryl alkyl ether), 1101.15 (C—O of secondary hydroxyl), 885.53 and 794.61 (1,2,4-trisubstituted); 3050 (backbone of naphthalene), 798.69, 780.62 (monosubstituted naphthalene ring);

$^1$HNMR (400 MHz, $CD_3COCD_3$) δ: 6.75-8.30 (m, 10H, Ar—H), 6.13 (s, 2H, —$OCH_2O$—), 3.55 (m, 2H, —$CH_2$ (NH)—), 4.55 (m, 1H, —COCH(OH)—), 4.35 (m, 1H, —CH(OH)—), 4.02 (q, 2H, —$OCH_2$—), 2.90-3.07 (m, 2H, -$PhCH_2$—);

$^{13}$CNMR (500 MHz, $CD_3COCD_3$) δ: 41.7, 45.1, 68.5, 71.3, 73.3, 101.2, 104.3, 112.7, 115.2, 120.4, 121.0, 122.2, 125.4, 126.1, 126.6, 127.4, 127.6, 132.7, 134.5, 146.0, 148.7, 156.8, 172.7.

EXAMPLE 12

Pharmacodynamic Test

1. Effects of bornyl β-(3,4-dihydroxylphenyl)-α-hydroxylpropionate Ester (Hereinafter Briefly Cited as "Bornyl Salvianate Ester") on Blood Flow of Cerebral Microcirculation in Rats with Middle Cerebral Artery Occlusion 60 SD rats with a body weight of 220±20 g were randomly divided into normal control group, model control group, salvianic acid injection group (ip. 1 mL/kg), and group of bornyl β-(3,4-dihydroxylphenyl)-α-hydroxylpropionate ester at a small, middle and large dose respectively (ip. 5, 15, and 35 mg/kg). The rats of normal group and model group were administered with equal-volume of physiologic saline by ip. The rats were anesthetized by intraperitoneal injection of 1% pentobarbital sodium at an amount of 40 mg/kg, then placed at supine position, head fixed, and cut skin along cervical middle line. Trachea cannula, was inserted into the rats and they were allowed to spontaneous respire. Right common jugular vein and common carotid artery were isolated and a suture was introduced for later use. Animals were fixed on a rat stereotaxic apparatus, a cranial window with a size of 6×8 mm was opened at the right temple with a dental drill, after hemostasis, cerebral dura mater was cut open with scissors to expose cerebral pia mater. The window was covered and sealed with glass and dental cement, and the laser probe of a laser-doppler microcirculatory blood flow meter was fixed on the cranial window. Then the animals were fixed at lateral position, the right common carotid artery was lifted, ligated at the proximal part and carefully cut with scissors, a nylon suture having a diameter of about 0.3 mm was introduced into the artery. The distance between the artery cut and the paropia of the rats was marked before the suture was introduced. When the nylon suture was introduced to approach the marked position, the speed for introducing the suture should slow down and the cerebral microcirculatory blood flow exhibited by the laser-doppler microcirculatory blood flow meter should be observed simultaneously. When the suture arrived at middle cerebral artery, an abrupt decrease of the microcirculatory blood flow would be observed. After the observation of a decrease in the microcirculatory blood flow, the suture was further penetrated by about 1 mm, and the distal end of the cut and the suture in the artery were ligated securely. Spare suture was cut-off. After the end of the test, it was checked whether the nylon suture blocked the initiation site of the middle cerebral artery, and the data of any animal whose artery was not blocked were cancelled. The animals of the control group were not treated. After the cranial window was prepared, the probe of J I2200 type laser-doppler microcirculatory blood flow meter was fixed at the cranial window, and the probe was maintained without displacement and rotation during the whole test. The microcirculatory blood flows before ligation and 5, 15, 30, 45 and 60 min after ligation were recorded, and the data of the animals in the drug-treatment groups were recorded at the same time points. The mean microcirculatory blood flow observed within 1 min at each time point was designated as the microcirculatory blood flow of the respective time point.

TABLE 1

Effects on cerebral microcirculatory blood flow in rats with middle cerebral artery occlusion (n = 10)

| Group | Dose | Microcirculatory blood flow (mL) | | | | |
|---|---|---|---|---|---|---|
| | | 5 min | 15 min | 30 min | 45 min | 60 min |
| Control | / | 65.3 ± 5.7 | 67.4 ± 7.4 | 67.8 ± 6.8 | 65.1 ± 5.9 | 64.2 ± 8.5 |
| Model | / | 10.2 ± 2.3 | 11.4 ± 3.4 | 13.2 ± 4.1 | 14.0 ± 3.4 | 14.9 ± 6.5 |
| Salvianic acid | 1 mL/kg | 10.8 ± 3.6 | 20.1 ± 6.9** | 31.2 ± 9.5** | 33.0 ± 6.8** | 29.4 ± 6.9** |
| Test Drug | 5 mg/kg | 11.4 ± 5.4 | 12.4 ± 4.6 | 12.9 ± 5.1 | 16.1 ± 4.1 | 16.0 ± 6.9 |
| Test Drug | 15 mg/kg | 9.4 ± 3.7 | 12.8 ± 5.6 | 20.7 ± 3.2* | 25.0 ± 5.2** | 24.4 ± 4.8** |
| Test Drug | 35 mg/kg | 10.8 ± 2.7 | 19.4 ± 5.1** | 32.7 ± 6.2** | 35.4 ± 8.2** | 35.2 ± 5.8** |

In comparison with the model group:
*P < 0.05,
**P < 0.01

The test results showed that, after the middle cerebral artery was blocked, the cerebral microcirculatory blood flow in blood-supply region (frontal and parietal lobe) decreased rapidly and kept at a relatively low level. Only after the artery was blocked for 30 min did the cerebral microcirculatory blood flow increase slightly, which indicated that cerebral ischemia models were successfully established. Meanwhile the cerebral microcirculatory blood flow increased slightly 30 minutes or 15 minutes after the administration of bornyl β-(3,4-dihydroxylphenyl)-α-hydroxylpropionate ester at 15 mg/kg and 35 mg/kg respectively. These results suggest the ditation of arteriole, and the increase of microcirculatory blood flow may have possible positive effects on ischemic cerebrovascular diseases, but the corresponding action mechanism needs to be investigated.

2. Protection Effects of Bornyl Salvianate Ester on Cardiac Ischemia Reperfusion (I/R) Injury 52 SD rats having a body weight of 220±20 g were randomly divided into model control group, salviannic acid injection group (in 1 mL/kg), and group of bornyl β-(3,4-dihydroxylphenyl)-α-hydroxylpropionate ester at a small, middle and large dose (ip 5, 15, 35 mg/kg). The rats of the normal group and the model control group were ip administered with equal-volume of physiologic saline. The rats of all groups were administered for consecutive 5 days. When the rats were administered for the last time, they were simultaneously anesthetized with 1.5% pentobarbital sodium (ip 45 mg/kg), then a catheter was inserted into the right carotid artery, and connected via a transducer to an eight-channeled physiological recorder. Tracheal cannula was performed, and the ventilation rate was maintained at 60 times/min. The chest was opened, a 6/0 suture was used to form a loop at a site 1~2 mm from the root of the anterior descending coronary artery, and a plastic pipe was introduced through the loop, then the loop was tightened up. The change of electrocardiogram was observed. An increase or decrease of ST indicated the success of ligation. The color of the myocardial tissue below the ligation suture became darker. 30 minutes later, the plastic pipe was pulled out to allow coronary artery blood flowing again and cause hyperemia of local tissue during reperfusion. For the groups subjected to ischemia for 30 min and reperfusion for 30 min, the myocardial infarction areas were recorded before the test, after ischemia for 1 min and 30 min, and after reperfusion for 30 min; for the groups subjected to ischemia for 30 min and reperfusion for 2 h, cardiac tissue samples were taken and fixed using 10% formalin, embedded with paraffin, serially sliced into sections with a thickness of 4 μm, and separately subjected to immunohistochemistry tests; the rats of the sham operation group were subjected only to the introduction of suture but their coronary arteries were not ligated.

Effects on Myocardial Infarct Areas Caused by Cardiac Muscle I/R

After the rats were subjected to ischemia and reperfusion for 30 minutes, their anterior descending coronaries were ligated again, then they were sacrificed, their hearts were removed promptly, and 0.5 mL of 1% evans blue was injected into heart chambers via aorta to distinguish the ischemic regions and the non-ischemic regions. After the heart atrium and right ventricle were cut-off, the heart was refrigerated at −20° C. for 30 min, then placed in a tailor-made slice groove, and cut along the long axis to form 2 mm slices. The slices were immersed in 1% TTC phosphoric acid buffer solution (pH7.4), and incubated at 37° C. for 30 min to distinguish risky regions and necrotic regions. Then the slices were fixed with 10% formaldehyde for 24 h to enhance staining color for contrast photography. After the above treatment, the myocardial tissue was divided into: normal myocardia in blue, ischemic myocardia in light red, and necrotic myocardion in gray. A computer image analysis software was used to calculate the percentage of the area of the infarct myocardial region (nec) based on the area of the risky myocardial region (aar, i.e., ischemic myocardia, including ischemic infarct region and ischemic non-infarct region) (nec/aar), and the percentage of the area of the infarct myocardial region based on the whole area of the myocardia (nec/lv) to indicate the degree of infarct, as well as the percentage of the area of the risky myocardia based on the area of the left ventricle (aar/lv).

TABLE 2

Effects on myocardial infarction areas caused by cardiac muscle I/R

| Group | Dose | Animal Number | aar/lv (%) | nec/lv (%) | nec/aar (%) |
|---|---|---|---|---|---|
| Model control | / | 12 | 67.10 ± 11.40 | 50.52 ± 15.65 | 64.10 ± 13.03 |
| Salvianic acid | 1 mL/kg | 10 | 50.21 ± 7.10* | 41.41 ± 5.49* | 49.87 ± 7.83* |
| Test drug | 5 mg/kg | 9 | 64.09 ± 18.10 | 48.45 ± 17.11 | 61.72 ± 14.65 |
| Test drug | 15 mg/kg | 10 | 63.02 ± 15.98 | 48.23 ± 15.34 | 62.63 ± 13.82 |
| Test drug | 35 mg/kg | 11 | 51.97 ± 13.04* | 40.21 ± 12.65* | 50.01 ± 9.03* |

In comparison with the model control group:
*P < 0.05

The results showed that, in comparison with the model control group, the values of aar/lv, nec/lv and nec/aar in the large dose group respectively decreased by 22.5%, 20.4% and 22% (P<0.01), suggesting that the area of the myocardial infarct caused by myocardia I/R can be lowered.

Effects on the Protein Expression of Bax, Bcl-2, Caspase-3, MMP-2 and PPARγ

Standard immunohistochemistry ABC and SP methods were employed for staining. Bax: anti-rabbit polyclonal antibody (Santa CruzBio. Inc.) at a dilution of 1:200; Bcl22: anti-rabbit polyclonal antibody (TBD Tianjin Biotechnological Center). At a dilution of 1100; caspase-3: anti-rabbit polyclonal antibody (Normarkers Fromont, Calif.), at a dilution of 1:200; MMP-2: anti-murine monoclonal antibody (NormarkersFromont, Calif.) at a dilution of 1:200; PPARγ: anti-caprine polyclonal antibody (Santa Cruz Bio. Inc.), at a dilution of 1:500. The specific procedures were performed in accordance with the instructions of the ABC and SP kits, DAB was used for color development, and neutral resin was used for mounting. PBS was used instead of the first antibody as a negative control. Cells with positive expression of the test polypeptides were of brown-yellow color, with MMP-2 protein being present in acytoplasm, Bcl-2 expressed in nuclear membrane and cytoplasm, Bax mainly in cytoplasm and partially in nucleus, and caspase-3 mainly in nucleus and partially in cytoplasm. CMIAS image analysis system was used for random selection of fields of slices and automatic selection of sites for analysis, and statistic analysis was performed by using mean optical density values or integral optical density values of the obtained myocardial tissue slices.

reduce the expression of Bax and caspase-3 proteins and increase the expression of Bcl-2 protein, suggesting that bornyl β-(3,4-dihydroxylphenyl)-α-hydroxylpropionate ester could initiate the self-protective mechanism of cells against injury by inducing the expression of Bcl-2 and reducing the levels of Bax and caspase-3, reverse the cell apoptosis and necrosis processed stimulated by the myocardiac I/R, thereby exhibit protection effects on myocardial cells.

MMP-2 is associated with cardiac muscle I/R injury, which is achieved by the cleavage of troponin I, which in turn would directly lead to cell apoptosis. MMP-2 specific inhibitor could improve the cardiac function of rats with myocardiac I/R, and the test results indicated that bornyl β-(3,4-dihydroxylphenyl)-α-hydroxylpropionate ester could cause the decrease of MMP-2 protein, which could be another mechanism for bornyl β-(3,4-dihydroxylphenyl)-α-hydroxylpropionate ester to protect myocardia from I/R injury.

3. Effects of Bornyl Salvianate Ester on Blood Pressure and Left Ventricular Function of Anesthetized Rats Rats were anesthetized by intraperitoneal injection of 20% urethane 5 mL/kg and fixed; the skin of neck of rats were incised, anterior cervical muscles were isolated, trachea was exposed, and tracheal cannula was inserted; common carotid artery was isolated, a cardiac catheter was introduced through the common carotid artery into left ventricle, the left intraventricular pressure was measured with a pressure transducer (T-200) of RM-6000 multi-channel polygraph and the carrier

TABLE 3

Effects on the protein expression of Bax, Bcl-2, caspase-3, MMP-2, and PPARγ (n = 10)

| | | OD value | | | | |
|---|---|---|---|---|---|---|
| Group | Dose | Bax | Bcl-2 | Caspase-3 | MMP-2 | PPARγ |
| Model control | / | 0.13 ± 0.04 | 0.14 ± 0.03 | 0.37 ± 0.11 | 0.16 ± 0.04 | 0.17 ± 0.02 |
| Salvianic acid | 1 mL/kg | 0.08 ± 0.02* | 0.18 ± 0.04 | 0.21 ± 0.12** | 0.12 ± 0.05 | 0.34 ± 0.08** |
| Test drug | 5 mg/kg | 0.12 ± 0.03 | 0.15 ± 0.03 | 0.35 ± 0.14 | 0.14 ± 0.05 | 0.16 ± 0.05 |
| Test drug | 15 mg/kg | 0.09 ± 0.05 | 0.15 ± 0.06 | 0.32 ± 0.08 | 0.14 ± 0.03 | 0.18 ± 0.06 |
| Test drug | 35 mg/kg | 0.07 ± 0.03* | 0.21 ± 0.04* | 0.20 ± 0.07** | 0.11 ± 0.03* | 0.18 ± 0.10 |

In comparison with the model control group:
*P < 0.05,
**P < 0.01

The results showed that the expression of Bcl-2 and Bax was indeed changed in the myocardial cells I/R, indicating that they participate in the regulation of cell apoptosis. Bornyl β-(3,4-dihydroxylphenyl)-α-hydroxylpropionate ester could amplifier (AP-601G) of RM-6000 multi-channel polygraph, then the signals of the left intraventricular pressure were input to the differential amplifier (ED-601G) of RM-6000 multi-channel polygraph to record the maximum rate of increasing and decreasing the left intraventricular pressure ($dp/dt_{max}$–$dp/dt_{max}$); right femoral artery was isolated, the arterial blood pressure was measured by using cannula; a recording electrode of electrocardiograph was connected to record type II electrocardiogram. All data were input into PowerLab/8Sp data acquisition and processing system via RM-6000 multichannel polygraph, and recorded, analyzed and processed by PowerLab/8Sp.

The abdomen was opened 1.5 cm below xiphoid bone to isolate duodenum, a small incision was formed on the duodenum away from blood vessels by ophthalmic scissors, a catheter was inserted and the incision was fixed by suture for administration. After the end of operation and a further waiting period of 30 min, normal data were recorded once the indexes to be monitored were stable.

Test drugs were duodenally administered via the catheter, and the indexes were monitored 5, 15, 30, 60, 90 and 120 min after the administration. The change ratios of the indexes were calculated in accordance with the following formula, and were used for statistic analysis among groups.

$$\text{Change\_ratio (\%)} = \frac{\left(\text{After\_administration} - \text{Before\_administration}\right)}{\text{Before\_administration}} \times 100$$

3.1 Effects on the Heart Rate of Anesthetized Rats

The test results indicated that the 4.5 mg/kg, 9 mg/kg and 18 mg/kg doses of bornyl salvianate ester showed no significant effects on the heart rate of anesthetized rats, no significant difference can be observed as compared to the blank control group; while verapamil hydrochloride significantly reduced the heart rate and significant difference can be observed as compared to the model group ($P<0.05$ or $P<0.01$) (Table 4).

3.2 Effects on Mean Arterial Pressure, Systolic Pressure and Diastolic Pressure of Anesthetized Rats In the group at the does of 18 mg/kg bornyl salvianate ester, the mean arterial pressure, systolic pressure and diastolic pressure of anesthetized rats significantly decreased after administration, and significant differences ($P<0.05$ or $P<0.01$) as compared to the blank control group were observed at the timepoints of 15, 60, 90 and 120 min; in the 9 mg/kg group of bornyl salvianate ester, the mean arterial pressure, systolicsystolic pressure and diastolic pressure of anesthetized rats exhibited a decrease tendency, and significant differences ($P<0.05$ or $P<0.01$) from the blank control group were observed at 15 and 60 min; in the 4.5 mg/kg group of bornyl salvianate ester, the mean arterial pressure, systolicsystolic pressure and diastolic pressure of anesthetized rats exhibited no significant change, and no significant difference from the blank control group were observed; while verapamil hydrochloride could significantly reduce the mean arterial pressure, systolicsystolic pressure and diastolic pressure of anesthetized rats, and significant differences ($P<0.01$) from the model control group were observed at 5, 15, 30, 60, 90 and 120 min (Tables 5, 6 and 7).

3.3 Effects on Left Intraventricular Pressure of Anesthetized Rats

In the 18 mg/kg group of bornyl salvianate ester, the left intraventricular pressure of anesthetized rats significantly decreased after administration, and significant differences ($P<0.05$ or $P<0.01$) from the blank control group were observed at 15, 30, 60, 90 and 120 min; in the 9 mg/kg group of bornyl salvianate ester, the left intraventricular pressure of anesthetized rats exhibited a decrease tendency, and significant differences ($P<0.05$ or $P<0.01$) from the blank control group were observed at 60 min; in the 4.5 mg/kg group of bornyl salvianate ester, the left intraventricular pressure of anesthetized rats was not significantly affected after administration, and no significant difference from the blank control group was observed; while verapamil hydrochloride significantly reduced the left intraventricular pressure of anesthetized rats, and significant differences ($P<0.01$) from the model control group were observed (Table 8).

3.4 Effects on dp/dt and –dp/dt of Anesthetized Rats

In the 18 mg/kg group of bornyl salvianate ester, the dp/dt of anesthetized rats significantly decreased after administration, and significant differences ($P<0.05$ or $P<0.01$) from the blank control group were observed at 15, 30, 60, 90 and 120 min; in the 9 mg/kg group of bornyl salvianate ester, the dp/dt of anesthetized rats exhibited a decrease tendency, and significant differences ($P<0.05$ or $P<0.01$) from the blank control group were observed at 60 and 120 min; in the 4.5 mg/kg group of bornyl salvianate ester, the dp/dt of anesthetized rats was not significantly affected after administration, and no significant difference from the blank control group was observed; while verapamil hydrochloride significantly reduced the dp/dt of anesthetized rats, and significant differences ($P<0.01$) from the model control group were observed.

In the 9 mg/kg and 18 mg/kg groups of bornyl salvianate ester, the –dp/dt of anesthetized rats exhibited a decrease tendency, and significant differences ($P<0.05$ or $P<0.01$) from the blank control group were observed at 60 and 120 min; in the 4.5 mg/kg group of bornyl salvianate ester, the –dp/dt of anesthetized rats was not significantly affected after administration, and no significant difference from the blank control group was observed; while verapamil hydrochloride significantly reduced the –dp/dt of anesthetized rats, and significant differences ($P<0.01$) from the model control group were observed (Tables 9, 10).

The test results indicate that bornyl salvianate ester could reduce left intraventricular pressure, dp/dt and –dp/dt, which suggests that bornyl salvianate ester has effects of reducing the negative cardiac efficiency of myocardial contractility, and the effects on negative cardiac efficiency could be the reason of the decrease of the mean arterial pressure, systolic pressure and diastolic pressure of anesthetized rats.

In the meantime, the test results showed that the $dp/dt_{MAX}$ decreased, but the heart rate did not change significantly, i.e., the $dp/dt_{MAX}$ was not in direct correlation with the heart rate. The mechanism for these phenomena needs further studying.

4. Protective Effects of Bornyl Salvianate Ester on Acute Myocardial Ischemia in Rats 60 Male rats were randomly divided into sham operation group (0.5% Poloxamer, 10 mL/kg), model control group (0.5% Poloxamer, 10 mL/kg), verapamil group (verapamil tablet, 10 mg/kg), and bornyl salvianate ester groups (10 mg/kg, 20 mg/kg and 40 mg/kg). At 0.5 h after the rats of these groups were administered intragastrically, the standard II lead electrocardiogram (before modeling) was recorded, and the height of ST-T segment was measured. The rats of sham operation group were then subjected to coronary artery braid without ligation, and the rats of other groups were subjected to coronary artery ligation in accordance with the following method to establish cute myocardial ischemia models. The rats were subjected to etherization, fixed at supine position, and their normal electrocardiograms (before modeling) were recorded. The skin of left thorax was incised under aseptic conditions, the 4$^{th}$ intercostal muscles were isolated in blunt way, the heart was extruded by light pressure to the right thorax, the left anterior descending coronary artery was ligated at a position 2~3 mm departing from the left coronary artery origin and between the pulmonary conus and the left auricle of heart, then the heart was sent back to thorax cavity immediately and sutured the incision. Penicillin was smeared topically for the prevention of infections. After operation, the electrocardiogram of postischemia was recorded immediately (at 0 min after modeling), and the height of ST-T segment was measured. At 24 h after the animals of these groups underwent the operation, they were anesthetized by peritoneal injection of 20% urethane 5 mL/kg, and the electrocardiogram was recorded again (at 24 h after modeling), and the height of ST-T segment was measured; blood samples were drawn from abdominal aorta, sera were separated, and the activities of lactate dehydrogenase (LDH), creatine kinase (CK), creatine kinase isoenzyme (CK-MB) and superoxide dismutase (SOD) and the content of malondialdehyde (MDA) were measured; the heart was taken out by open chest and washed with cold physiological saline, the heart atrium was removed, the heart ventricle was cross cut to form 3~4 slices, the slices were dipped in 0.25% NBT solution and stained under 37° C. water-bath for 10 min, the infarct cardiac muscles were cut and weighed, and the weight percentage of the infarct cardiac muscles based on the cardiac muscles of the whole heart ventricle was calculated (Tables 11-14).

The results showed that in all the bornyl-salvianate-ester dosed groups, the proportion of the infarct cardiac muscles in the whole ventricle was reduced, in which relative potent effects were observed in the middle and large dose groups (P<0.05 or P<0.01); in all dose groups, the activities of lactate dehydrogenase (LDH), creatine kinase (CK), creatine kinase isoenzyme (CK-MB) decreased 24 h later; the superoxide dismutase (SOD) in rats with acute myocardial ischemia increased, especially in the large dose group (P<0.05); in middle and large dose groups, a decrease tendency of the serum MDA content was observed, but no significant difference from the model control group was observed; at 24 h after coronary artery ligation, the ST-T segment elevation in the electrocardiogram was observed, especially in the large dose group (P<0.05). The results indicated that the bornyl salvianate ester could reduce the area of myocardial infarction in rats, and exhibit protective effects on acute myocardial ischemia in rats.

TABLE 4

Effects on heart rate (beat/min)

| Group | Dose | Before administration | After administration 5' | 15' | 30' | 60' | 90' | 120' |
|---|---|---|---|---|---|---|---|---|
| Blank control (n = 10) | 2.5 mL/kg | 344.39 ± 42.73 | 344.28 ± 46.02<br>2.23 ± 5.30 | 355.13 ± 44.09<br>5.66 ± 7.27 | 349.22 ± 47.61<br>4.44 ± 10.34 | 354.23 ± 47.61<br>6.18 ± 11.78 | 361.39 ± 48.94<br>8.06 ± 15.53 | 359.78 ± 54.27<br>7.37 ± 15.32 |
| Tween control (n = 10) | 2.5 mL/kg | 322.67 ± 58.28 | 326.83 ± 50.06<br>2.42 ± 11.78 | 328.47 ± 46.72<br>4.05 ± 20.61 | 337.91 ± 49.80<br>6.63 ± 18.47 | 332.98 ± 55.18<br>5.03 ± 19.64 | 333.84 ± 54.39<br>5.46 ± 19.62 | 327.03 ± 57.06<br>3.30 ± 20.73 |
| Propanoid acid borneol ester (n = 10) | 18 mg/kg | 357.28 ± 36.29 | 358.56 ± 44.88<br>0.22 ± 4.94 | 356.00 ± 40.82<br>−0.07 ± 9.93 | 348.07 ± 39.21<br>−2.01 ± 12.45 | 357.22 ± 47.10<br>0.39 ± 13.05 | 355.33 ± 9.61<br>−0.44 ± 6.91 | 357.68 ± 53.26<br>0.28 ± 12.04 |
| Propanoid acid borneol ester (n = 10) | 9 mg/kg | 373.43 ± 41.28 | 374.04 ± 47.60<br>0.28 ± 7.83 | 374.93 ± 47.51<br>0.48 ± 7.36 | 361.94 ± 43.56<br>−3.00 ± 5.83 | 359.61 ± 39.30<br>−4.52 ± 7.13 | 354.38 ± 62.30<br>−4.13 ± 17.94 | 354.09 ± 47.98<br>−4.62 ± 12.34 |
| Propanoid acid borneol ester (n = 10) | 4.5 mg/kg | 329.43 ± 43.77 | 337.41 ± 47.67<br>2.49 ± 7.18 | 347.56 ± 47.18<br>5.67 ± 7.58 | 348.91 ± 52.11<br>5.97 ± 9.72 | 365.43 ± 32.77<br>12.05 ± 12.32 | 369.71 ± 35.54<br>13.31 ± 13.05 | 360.36 ± 51.93<br>9.40 ± 6.30 |
| Verapamil control (n = 10) | 11.4 mg/kg | 363.19 ± 46.67 | 345.03 ± 33.81<br>−4.63 ± 4.08** | 324.96 ± 36.20<br>−9.67 ± 11.64** | 322.02 ± 51.09<br>−10.32 ± 16.56* | 317.91 ± 58.04<br>−11.31 ± 19.30* | 329.61 ± 55.70<br>−7.75 ± 20.11 | 328.05 ± 58.98<br>−7.96 ± 21.39 |

In comparison with the Tween control group:
*p < 0.05,
**p < 0.01

TABLE 5

Effects on contractive pressure (mmHg)

| Group | Dose | Before administration | After administration 5' | 15' | 30' |
|---|---|---|---|---|---|
| Blank control (n = 10) | 2.5 mL/kg | 117.57 ± 21.61 | 121.76 ± 23.27<br>3.55 ± 5.90 | 123.75 ± 26.54<br>4.98 ± 9.25 | 118.91 ± 32.99<br>−0.09 ± 15.39 |
| Tween control (n = 10) | 2.5 mL/kg | 124.41 ± 26.13 | 122.64 ± 26.97<br>−1.33 ± 6.67 | 124.75 ± 24.75<br>1.08 ± 9.91 | 121.92 ± 23.44<br>−0.79 ± 13.70 |

TABLE 5-continued

Effects on contractive pressure (mmHg)

| Group | Dose | Before admin | 5' | 15' | 30' |
|---|---|---|---|---|---|
| Propanoid acid borneol ester (n = 10) | 18 mg/kg | 128.25 ± 23.86 | 128.34 ± 28.96 −0.06 ± 12.42 | 120.90 ± 26.54 −5.49 ± 14.53* | 117.76 ± 22.90 −7.74 ± 12.22 |
| Propanoid acid borneol ester (n = 10) | 9 mg/kg | 132.26 ± 20.00 | 131.10 ± 24.38 −1.14 ± 6.68 | 127.85 ± 23.92 −3.57 ± 7.14* | 122.58 ± 23.46 −7.38 ± 8.66 |
| Propanoid acid borneol ester (n = 10) | 4.5 mg/kg | 129.06 ± 22.13 | 126.54 ± 25.94 −1.96 ± 11.16 | 128.80 ± 24.39 −0.05 ± 10.13 | 129.90 ± 23.86 0.93 ± 11.47 |
| Verapamil control (n = 10) | 11.4 mg/kg | 137.10 ± 28.79 | 115.30 ± 19.35 −14.92 ± 9.40** | 98.48 ± 16.13 −26.88 ± 11.21** | 94.47 ± 17.17 −29.86 ± 12.10** |

| | | After administration | | |
|---|---|---|---|---|
| | Group | 60' | 90' | 120' |
| | Blank control (n = 10) | 118.80 ± 31.50 0.07 ± 10.36 | 118.40 ± 33.16 −0.17 ± 12.98 | 124.51 ± 35.18 5.80 ± 24.03 |
| | Tween control (n = 10) | 120.80 ± 29.92 −2.46 ± 16.70 | 121.05 ± 27.12 −1.80 ± 16.77 | 119.48 ± 25.05 −2.7 ± 17.49 |
| | Propanoid acid borneol ester (n = 10) | 106.97 ± 32.22 −16.34 ± 19.90* | 104.23 ± 32.16 −18.68 ± 18.21** | 113.34 ± 24.47 −10.88 ± 16.04* |
| | Propanoid acid borneol ester (n = 10) | 115.46 ± 23.90 −12.63 ± 11.39** | 120.90 ± 31.83 −8.80 ± 16.65 | 120.85 ± 32.13 −9.19 ± 14.65* |
| | Propanoid acid borneol ester (n = 10) | 135.97 ± 22.80 5.64 ± 8.91 | 131.95 ± 25.10 2.56 ± 13.11 | 128.62 ± 28.30 −0.49 ± 12.28 |
| | Verapamil control (n = 10) | 98.49 ± 22.31 −26.55 ± 17.97** | 99.15 ± 23.91 −26.28 ± 17.28** | 102.58 ± 27.01 −23.82 ± 18.16** |

In comparison with the Tween control group:
*p < 0.05,
**p < 0.01

TABLE 6

Effects on diastolic pressure (mmHg)

| Group | Dose | Before administration | After administration 5' | 15' | 30' |
|---|---|---|---|---|---|
| Blank control (n = 10) | 2.5 mL/kg | 63.92 ± 12.98 | 66.51 ± 13.71 4.05 ± 6.32 | 68.12 ± 15.60 6.28 ± 10.50 | 66.35 ± 18.40 2.60 ± 16.02 |
| Tween control (n = 10) | 2.5 mL/kg | 67.56 ± 14.29 | 66.26 ± 14.25 −1.57 ± 8.21 | 67.66 ± 13.23 1.46 ± 14.24 | 66.42 ± 13.11 0.13 ± 18.94 |
| Propanoid acid borneol ester (n = 10) | 18 mg/kg | 73.04 ± 11.87 | 72.55 ± 16.58 −1.00 ± 14.79 | 68.87 ± 14.57 −5.45 ± 15.82* | 66.68 ± 11.95 −7.68 ± 16.90 |
| Propanoid acid borneol ester (n = 10) | 9 mg/kg | 69.21 ± 15.19 | 68.02 ± 18.77 −2.47 ± 10.80 | 66.18 ± 19.00 −5.33 ± 9.64* | 62.90 ± 17.46 −9.50 ± 10.75* |
| Propanoid acid borneol ester (n = 10) | 4.5 mg/kg | 68.47 ± 11.97 | 68.68 ± 15.82 −0.08 ± 12.81 | 70.87 ± 15.08 3.38 ± 12.17 | 71.78 ± 15.67 4.78 ± 14.39 |
| Verapamil control (n = 10) | 11.4 mg/kg | 75.39 ± 19.27 | 59.69 ± 12.55 −19.04 ± 12.70** | 50.08 ± 9.88 −31.18 ± 15.04** | 48.00 ± 9.98 −33.98 ± 15.67** |

| | | After administration | | |
|---|---|---|---|---|
| | Group | 60' | 90' | 120' |
| | Blank control (n = 10) | 66.54 ± 17.95 3.59 ± 15.55 | 66.18 ± 8.51 3.24 ± 17.92 | 68.44 ± 20.16 6.54 ± 23.33 |
| | Tween control (n = 10) | 65.95 ± 16.45 −1.21 ± 21.94 | 66.05 ± 15.27 −0.75 ± 21.63 | 65.27 ± 14.84 −1.67 ± 22.83 |
| | Propanoid acid borneol ester (n = 10) | 60.98 ± 16.13 −15.66 ± 21.14* | 60.29 ± 15.88 −16.74 ± 18.37* | 61.54 ± 13.73 −14.64 ± 19.58* |
| | Propanoid acid borneol ester (n = 10) | 59.10 ± 16.07 −14.30 ± 13.75** | 63.12 ± 19.81 −8.83 ± 17.11 | 62.58 ± 22.20 −10.28 ± 17.60* |
| | Propanoid acid borneol ester (n = 10) | 76.78 ± 14.34 12.13 ± 9.39 | 74.71 ± 18.13 8.47 ± 17.66 | 72.46 ± 20.46 4.39 ± 16.80 |
| | Verapamil control (n = 10) | 48.81 ± 11.47 −32.54 ± 19.02** | 49.38 ± 13.27 −32.10 ± 18.74** | 51.84 ± 13.93 −29.18 ± 17.73** |

In comparison with the Tween control group:
*p < 0.05,
**p < 0.01

TABLE 7

Effects on mean arterial pressure (mmHg)

| Group | Dose | Before administration | After administration 5' | After administration 15' | After administration 30' |
|---|---|---|---|---|---|
| Blank control (n = 10) | 2.5 mL/kg | 81.80 ± 15.30 | 84.93 ± 16.35<br>3.81 ± 6.04 | 86.66 ± 18.78<br>5.64 ± 9.78 | 83.87 ± 22.97<br>1.26 ± 15.60 |
| Tween control (n = 10) | 2.5 mL/kg | 86.51 ± 18.19 | 85.05 ± 18.38<br>−1.45 ± 7.32 | 86.69 ± 16.88<br>1.28 ± 12.05 | 84.92 ± 16.37<br>−0.32 ± 16.30 |
| Propanoid acid borneol ester (n = 10) | 18 mg/kg | 91.44 ± 15.44 | 91.15 ± 20.31<br>−0.58 ± 13.53 | 86.21 ± 18.29<br>−5.52 ± 14.99* | 83.71 ± 15.31<br>−7.79 ± 14.45 |
| Propanoid acid borneol ester (n = 10) | 9 mg/kg | 90.23 ± 16.25 | 89.05 ± 20.26<br>−1.79 ± 8.69 | 86.74 ± 20.25<br>−4.42 ± 8.30* | 82.79 ± 18.98<br>−8.42 ± 9.56 |
| Propanoid acid borneol ester (n = 10) | 4.5 mg/kg | 88.67 ± 14.74 | 87.97 ± 18.89<br>−1.01 ± 11.95 | 90.18 ± 17.91<br>1.66 ± 11.07 | 91.15 ± 17.95<br>2.91 ± 12.81 |
| Verapamil control (n = 10) | 11.4 mg/kg | 95.96 ± 22.22 | 78.22 ± 14.31<br>−17.07 ± 11.03** | 66.21 ± 11.57<br>−29.16 ± 13.09** | 63.49 ± 11.93<br>−32.04 ± 13.81** |

| Group | After administration 60' | After administration 90' | After administration 120' |
|---|---|---|---|
| Blank control (n = 10) | 83.96 ± 22.23<br>1.82 ± 12.68 | 83.59 ± 23.20<br>1.51 ± 15.15 | 87.13 ± 25.01<br>6.04 ± 22.99 |
| Tween control (n = 10) | 84.24 ± 20.76<br>−1.82 ± 19.29 | 84.38 ± 19.01<br>−1.26 ± 19.14 | 83.34 ± 18.04<br>−2.22 ± 20.12 |
| Propanoid acid borneol ester (n = 10) | 76.31 ± 21.36<br>−16.01 ± 20.44* | 74.94 ± 21.07<br>−17.64 ± 18.17* | 78.81 ± 17.04<br>−12.96 ± 17.66* |
| Propanoid acid borneol ester (n = 10) | 77.89 ± 18.11<br>−13.46 ± 12.43* | 82.38 ± 23.18<br>−8.77 ± 16.66 | 82.00 ± 25.04<br>−9.71 ± 15.95* |
| Propanoid acid borneol ester (n = 10) | 96.51 ± 16.69<br>8.95 ± 8.95 | 93.79 ± 20.11<br>5.62 ± 15.30 | 91.18 ± 22.76<br>2.06 ± 14.37 |
| Verapamil control (n = 10) | 65.37 ± 14.57<br>−29.68 ± 18.40** | 65.97 ± 16.34<br>−29.33 ± 17.82** | 68.75 ± 17.93<br>−26.65 ± 17.62** |

In comparison with the Tween control group:
*p < 0.05,
**p < 0.01

TABLE 8

Effects on left intraventricular pressure (mmHg)

| Group | Dose | Before administration | After administration 5' | After administration 15' | After administration 30' |
|---|---|---|---|---|---|
| Blank control (n = 10) | 2.5 mL/kg | 124.84 ± 14.88 | 127.99 ± 16.77<br>2.48 ± 4.20 | 128.87 ± 18.64<br>3.05 ± 5.46 | 126.10 ± 22.02<br>0.51 ± 8.27 |
| Tween control (n = 10) | 2.5 mL/kg | 126.46 ± 14.18 | 125.76 ± 13.38<br>−0.41 ± 4.07 | 127.22 ± 12.98<br>0.87 ± 6.22 | 125.33 ± 14.26<br>−0.61 ± 8.37 |
| Propanoid acid borneol ester (n = 10) | 18 mg/kg | 131.93 ± 16.79 | 131.90 ± 18.96<br>−0.01 ± 7.29 | 126.28 ± 18.51<br>−4.15 ± 8.95* | 124.81 ± 18.94<br>−5.46 ± 7.09 |
| Propanoid acid borneol ester (n = 10) | 9 mg/kg | 128.29 ± 18.38 | 128.87 ± 25.63<br>−0.03 ± 8.26 | 127.06 ± 25.57<br>−1.37 ± 9.10 | 123.59 ± 25.06<br>−4.07 ± 8.57 |
| Propanoid acid borneol ester (n = 10) | 4.5 mg/kg | 128.68 ± 20.18 | 128.67 ± 18.24<br>0.38 ± 6.72 | 130.13 ± 18.12<br>1.51 ± 6.25 | 129.67 ± 17.48<br>1.22 ± 7.07 |
| Verapamil control (n = 10) | 11.4 mg/kg | 137.79 ± 18.96 | 128.71 ± 14.20<br>−6.24 ± 4.79** | 120.22 ± 12.98<br>−12.21 ± 7.42** | 116.59 ± 13.59<br>−14.73 ± 8.91** |

| Group | After administration 60' | After administration 90' | After administration 120' |
|---|---|---|---|
| Blank control (n = 10) | 126.30 ± 21.69<br>0.75 ± 7.10 | 125.79 ± 22.94<br>0.27 ± 8.10 | 128.12 ± 24.71<br>2.02 ± 10.87 |
| Tween control (n = 10) | 124.91 ± 16.52<br>−1.07 ± 9.12 | 124.32 ± 15.43<br>−1.45 ± 9.18 | 122.50 ± 15.26<br>−2.83 ± 9.80 |
| Propanoid acid borneol ester (n = 10) | 120.67 ± 23.43<br>−8.71 ± 11.64* | 117.91 ± 22.68<br>−10.81 ± 11.60* | 119.85 ± 22.26<br>−9.13 ± 13.16** |
| Propanoid acid borneol ester (n = 10) | 119.77 ± 23.09<br>−6.84 ± 8.75* | 122.40 ± 26.58<br>−4.88 ± 11.37 | 121.85 ± 26.36<br>−5.47 ± 9.76 |
| Propanoid acid borneol ester (n = 10) | 134.39 ± 19.12<br>4.73 ± 6.55 | 130.91 ± 17.22<br>2.39 ± 9.41 | 129.15 ± 18.53<br>0.79 ± 7.76 |
| Verapamil control (n = 10) | 115.68 ± 15.37<br>−15.14 ± 12.14** | 115.10 ± 16.60<br>−15.59 ± 12.52** | 118.39 ± 16.55<br>−13.34 ± 11.53** |

In comparison with the Tween control group:
*p < 0.05,
**p < 0.01

TABLE 9

Effects on the change-rate of left intraventricular pressure MAX, (mmHg/s)

| Group | Dose | Before administration | After administration 5' | After administration 15' | After administration 30' |
|---|---|---|---|---|---|
| Blank control (n = 10) | 2.5 mL/kg | 5121.1 ± 940.7 | 5300.2 ± 1071.0<br>3.5 ± 8.2 | 5363.7 ± 1193.1<br>4.6 ± 10.9 | 5258.2 ± 1366.8<br>1.7 ± 13.5 |
| Tween control (n = 10) | 2.5 mL/kg | 5246.5 ± 14.18 | 5252.7 ± 13.38<br>1.3 ± 12.6 | 5408.4 ± 12.98<br>4.5 ± 18.3 | 5318.1 ± 14.26<br>2.5 ± 21.3 |
| Propanoid acid borneol ester (n = 10) | 18 mg/kg | 5695.0 ± 1086.8 | 5694.7 ± 1264.7<br>−0.3 ± 9.3 | 5470.3 ± 1416.7<br>−4.7 ± 11.8* | 5186.9 ± 1177.3<br>−8.9 ± 11.5* |
| Propanoid acid borneol ester (n = 10) | 9 mg/kg | 5435.8 ± 1200.0 | 5388.9 ± 1187.0<br>−0.7 ± 6.7 | 5321.6 ± 1133.0<br>−1.6 ± 7.4 | 5179.1 ± 1270.9<br>−5.0 ± 7.8 |
| Propanoid acid borneol ester (n = 10) | 4.5 mg/kg | 5380.2 ± 913.7 | 5429.3 ± 1279.7<br>0.4 ± 11.0 | 5435.9 ± 1216.6<br>0.9 ± 11.4 | 5408.8 ± 1352.2<br>0.1 ± 13.5 |
| Verapamil control (n = 10) | 11.4 mg/kg | 5455.9 ± 1418.1 | 4857.7 ± 1002.4<br>−9.7 ± 7.0** | 4284.9 ± 793.2<br>−19.6 ± 11.8** | 4152.8 ± 901.5<br>−22.1 ± 14.0** |

| Group | After administration 60' | After administration 90' | After administration 120' |
|---|---|---|---|
| Blank control (n = 10) | 5139.2 ± 926.2<br>0.9 ± 10.4 | 5094.3 ± 946.1<br>0.2 ± 12.7 | 5408.2 ± 1342.3<br>5.1 ± 14.8 |
| Tween control (n = 10) | 5269.2 ± 16.52<br>1.6 ± 21.5 | 5295.0 ± 15.43<br>2.0 ± 20.2 | 5205.3 ± 15.26<br>0.2 ± 21.8 |
| Propanoid acid borneol ester (n = 10) | 4905.3 ± 1047.7<br>−12.4 ± 18.7* | 4676.5 ± 941.1<br>−16.7 ± 15.5** | 5012.6 ± 777.5<br>−10.9 ± 12.4** |
| Propanoid acid borneol ester (n = 10) | 4966.9 ± 1297.4<br>−9.2 ± 10.0* | 5113.5 ± 1356.4<br>−6.4 ± 13.2 | 4959.8 ± 1399.0<br>−9.7 ± 11.2* |
| Propanoid acid borneol ester (n = 10) | 5760.1 ± 1393.5<br>7.1 ± 18.3 | 5706.1 ± 1390.6<br>7.6 ± 26.1 | 5512.7 ± 1250.1<br>3.6 ± 20.4 |
| Verapamil control (n = 10) | 3919.4 ± 784.0<br>−25.4 ± 17.3** | 3759.0 ± 814.5<br>−28.1 ± 19.0** | 4044.6 ± 844.9<br>−23.1 ± 18.4** |

In comparison with the Tween control group:
*$p < 0.05$,
**$p < 0.01$

TABLE 10

Effects on the change-rate of left intraventricular pressure, -MAX (mm/Hg/s)

| Group | Dose | Before administration | After administration 5' | After administration 15' | After administration 30' |
|---|---|---|---|---|---|
| Blank control (n = 10) | 2.5 mL/kg | −3790.6 ± 596.7 | −3865.0 ± 679.8<br>1.8 ± 4.8 | −3891.5 ± 775.2<br>2.3 ± 8.0 | −3879.0 ± 906.5<br>1.3 ± 11.4 |
| Tween control (n = 10) | 2.5 mL/kg | −3753.7 ± 603.1 | −3690.5 ± 526.4<br>−1.4 ± 2.7 | −3767.3 ± 551.9<br>0.9 ± 8.5 | −3692.4 ± 698.4<br>−1.0 ± 16.2 |
| Propanoid acid borneol ester (n = 10) | 18 mg/kg | −4092.0 ± 905.4 | −4103.4 ± 981.2<br>0.0 ± 7.8 | −3991.9 ± 948.6<br>−2.4 ± 9.3 | −3923.8 ± 879.8<br>−3.9 ± 8.2 |
| Propanoid acid borneol ester (n = 10) | 9 mg/kg | −3881.3 ± 735.6 | −3908.5 ± 1013.0<br>0.0 ± 11.2 | −3792.8 ± 979.5<br>−2.9 ± 10.2 | −3696.8 ± 997.3<br>−5.5 ± 10.8 |
| Propanoid acid borneol ester (n = 10) | 4.5 mg/kg | −4246.1 ± 669.3 | −4152.9 ± 764.8<br>−2.2 ± 8.2 | −4141.1 ± 755.6<br>−2.4 ± 9.1 | −4090.5 ± 704.6<br>−3.6 ± 6.5 |
| Verapamil control (n = 10) | 11.4 mg/kg | −4215.6 ± 1058.0 | −3812.9 ± 779.3<br>−8.5 ± 6.6** | −3548.9 ± 707.7<br>−14.5 ± 9.9** | −3416.6 ± 767.5<br>−17.8 ± 11.8** |

| Group | After administration 60' | After administration 90' | After administration 120' |
|---|---|---|---|
| Blank control (n = 10) | −3881.4 ± 781.9<br>2.0 ± 10.4 | −3858.7 ± 715.1<br>1.8 ± 10.9 | −3985.4 ± 899.9<br>4.4 ± 13.8 |
| Tween control (n = 10) | −3673.8 ± 721.5<br>−1.6 ± 16.5 | −3658.5 ± 653.0<br>−1.8 ± 16.4 | −3573.1 ± 702.5<br>−4.4 ± 15.4 |
| Propanoid acid borneol ester (n = 10) | −3744.3 ± 851.5<br>−7.9 ± 14.0* | −3659.3 ± 806.3<br>−9.2 ± 16.9 | −3692.1 ± 863.3<br>−8.8 ± 16.9* |
| Propanoid acid borneol ester (n = 10) | −3569.5 ± 857.8<br>−8.3 ± 10.2* | −3629.7 ± 1013.3<br>−7.2 ± 13.3 | −3541.7 ± 917.7<br>−9.2 ± 11.3* |
| Propanoid acid borneol ester (n = 10) | −4146.8 ± 820.5<br>−2.4 ± 10.2 | −4156.0 ± 947.7<br>−2.2 ± 15.9 | −3995.2 ± 837.9<br>−5.6 ± 14.3 |

TABLE 10-continued

Effects on the change-rate of left intraventricular pressure, -MAX (mm/Hg/s)

| | | | | |
|---|---|---|---|---|
| Verapamil control (n = 10) | −3436.8 ± 691.1 −16.2 ± 16.0** | −3247.4 ± 773.2 −20.9 ± 16.9** | −3452.2 ± 630.9 −16.3 ± 11.4** | |

In comparison with the Tween control group:
*$p < 0.05$,
**$p < 0.01$

TABLE 11

Effects on area of myocardial infarction in rats

| Group | Dose (mg/kg) | Animal number | Ventricle weight(g) | Non-infarct region weight (g) | Infarct region weight (g) | Percentage (%) |
|---|---|---|---|---|---|---|
| Sham operation | / | 10 | 0.66 ± 0.03 | | | |
| Model control | / | 10 | 0.68 ± 0.05 | 0.45 ± 0.03 | 0.23 ± 0.04 | 33.77 ± 4.31 |
| bornyl salvianate ester | 10 | 10 | 0.68 ± 0.09 | 0.47 ± 0.07 | 0.20 ± 0.05 | 30.09 ± 5.69 |
| bornyl salvianate ester | 20 | 10 | 0.68 ± 0.08 | 0.49 ± 0.09 | 0.18 ± 0.05* | 25.73 ± 6.35** |
| bornyl salvianate ester | 40 | 10 | 0.63 ± 0.07 | 0.45 ± 0.06 | 0.18 ± 0.04* | 28.95 ± 5.57* |
| Verapamil | 10 | 10 | 0.65 ± 0.09 | 0.46 ± 0.08 | 0.18 ± 0.04* | 27.60 ± 5.03** |

In comparison with the model control group:
*$P < 0.05$,
**$P < 0.01$

TABLE 12

Effects on the activities of serum LDH and CK in rats with myocardial ischemia

| Group | Dose (mg/kg) | Animal number | CK (U/L) | CK-MB (U/L) | LDH (U/L) |
|---|---|---|---|---|---|
| Sham operation | / | 10 | 653.1 ± 164.9** | 565.3 ± 122.2** | 1091.7 ± 259.7** |
| Model control | / | 10 | 1058.5 ± 150.0 | 1422.6 ± 182.3 | 2351.4 ± 220.83 |
| bornyl salvianate ester | 10 | 10 | 1214.2 ± 160.2* | 1267.0 ± 274.4 | 1663.7 ± 374.43** |
| bornyl salvianate ester | 20 | 10 | 894.5 ± 176.3* | 1074.1 ± 116.8** | 2022.7 ± 202.63** |
| bornyl salvianate ester | 40 | 10 | 778.0 ± 177.1** | 906.3 ± 99.9** | 1712.5 ± 209.1** |
| Verapamil | 10 | 10 | 752.2 ± 102.8** | 776.6 ± 127.6** | 1160.8 ± 145.0** |

In comparison with the model control group:
*$P < 0.05$,
**$P < 0.01$

TABLE 13

Effects on the activities of serum SOD and MDA in rats with myocardial ischemia

| Group | Dose (mg/kg) | Animal number | SOD (U/mL) | MDA (nmol/mL) |
|---|---|---|---|---|
| Sham operation | / | 10 | 155.08 ± 21.45** | 6.86 ± 5.67* |
| Model control | / | 10 | 95.46 ± 26.05 | 18.20 ± 12.10 |
| bornyl salvianate ester | 10 | 10 | 117.66 ± 31.97 | 21.69 ± 27.94 |
| bornyl salvianate ester | 20 | 10 | 111.32 ± 20.36 | 10.60 ± 11.156 |
| bornyl salvianate ester | 40 | 10 | 119.63 ± 23.53* | 9.43 ± 6.57 |
| Verapamil | 10 | 10 | 126.16 ± 28.10* | 11.86 ± 5.93 |

In comparison with the model control group:
*$P < 0.05$,
**$P < 0.01$

TABLE 14

Effects on the ST-T segment of ECG in rats with myocardial ischemia

| Group | Dose (mg/kg) | Animal Number | Elevation of ST-T segment (mV) | | |
|---|---|---|---|---|---|
| | | | Before modeling | 0 min after modeling | 24 h after modeling |
| Sham operation | / | 10 | 0.18 ± 0.08 | 0.15 ± 0.25 | 0.12 ± 0.06 |
| | | | Change rate (%) | 140.08 ± 161.56 | 22.34 ± 21.51** |
| Model control | / | 10 | 0.20 ± 0.09 | 0.19 ± 0.41 | 0.23 ± 0.10 |
| | | | Change rate (%) | 155.67 ± 158.10 | 92.67 ± 91.35 |
| bornyl salvianate ester | 10 | 10 | 0.21 ± 0.06 | 0.24 ± 0.24 | 0.17 ± 0.09 |
| | | | Change rate (%) | 95.00 ± 78.34 | 49.00 ± 36.27 |
| bornyl salvianate ester | 20 | 10 | 0.17 ± 0.07 | 0.13 ± 0.16 | 0.11 ± 0.10 |
| | | | Change rate (%) | 91.61 ± 116.85 | 60.77 ± 39.69 |
| bornyl salvianate ester | 40 | 10 | 0.21 ± 0.06 | 0.36 ± 0.17 | 0.18 ± 0.07 |
| | | | Change rate (%) | 103.87 ± 148.26 | 29.01 ± 18.99* |
| Verapamil | 10 | 10 | 0.23 ± 0.04 | 0.23 ± 0.12 | 0.18 ± 0.04 |
| | | | Change rate (%) | 34.36 ± 35.86* | 19.17 ± 20.94* |

In comparison with the model control group:
*$P < 0.05$,
**$P < 0.01$

What is claimed is:

1. A compound of the formula (I):

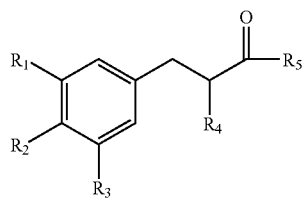

(I)

wherein $R_1$ and $R_2$ are OH, and $R_3$ is selected from the group consisting of H, OH, F, Cl, Br, methoxy and ethoxy; or alternatively, $R_1$ and $R_2$ together form —OCH$_2$O—, and $R_3$ is selected from the group consisting of H, OH, methoxy, ethoxy and halogens;

$R_4$ is OH or acyloxy; and $R_5$ is selected from cycloalkoxyl.

2. The compound according to claim 1, wherein $R_4$ is OH.

3. The compound according to claim 1, wherein $R_4$ is aroyloxy or heterocyclic radical-substituted acyloxy.

4. The compound according to claim 3, wherein $R_4$ is o-acetoxybenzoyloxy, 3-pyridinylbenzoyloxy or 4-pyridinylbenzoyloxy.

5. The compound according to any one of claims 1~4, wherein $R_5$ is:

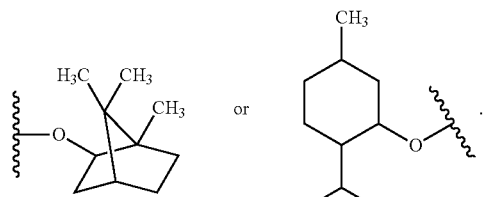

6. The compound according to claim 1, wherein $R_1$ and $R_2$ separately are OH.

7. The compound according to claim 1, wherein $R_1$ and $R_2$ together form —OCH$_2$O—.

8. The compound according to claim 6, wherein $R_3$=H, $R_4$=OH,

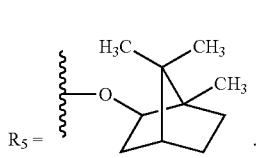

9. The compound according to claim 7, wherein $R_3$=H,

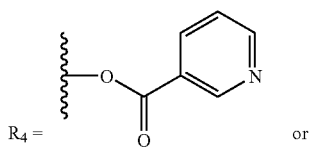

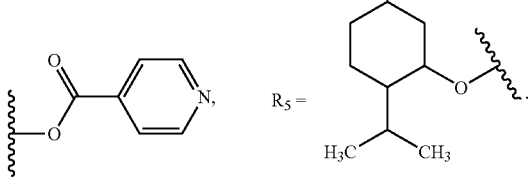

10. The compound according to claim 7, wherein $R_3$=H,

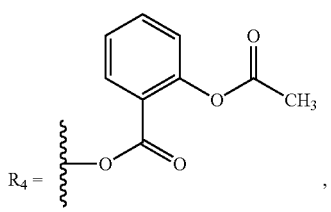

-continued

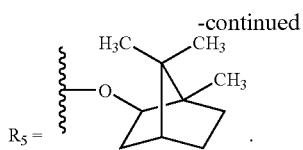

11. A process for synthesizing a compound according to claim 1, which comprises reacting a compound of formula (III) with a compound of formula (IV) or a hydrate thereof in the presence of a catalyst:

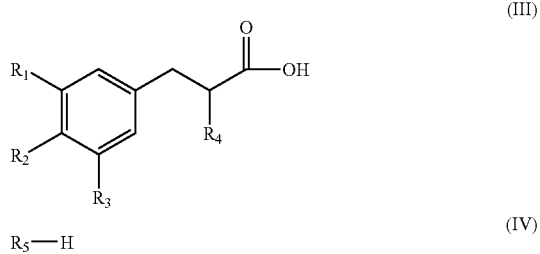

(III)

(IV)

wherein $R_1$, $R_2$, $R_3$, $R_4$ and $R_5$ have the same meanings as in the formula (I); or which comprises reacting a compound of the formula (V) with a compound of formula (VI) or a hydrate thereof in the presence of a catalyst:

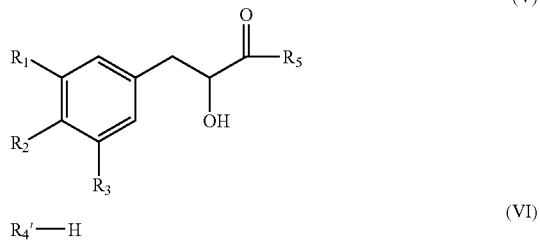

(V)

(VI)

wherein $R_1$, $R_2$, $R_3$ and $R_5$ have the same meaning as in the formula (I), and $R_4'$ is acyloxy.

12. The process according to claim 11, wherein the catalyst is concentrated $H_2SO_4$, silicotungstic acid, phosphomolybdic acid, p-toluene sulfonic acid, $S_2O_8^{2-}/ZrO_2$, aluminum trichloride, zinc chloride and/or magnesium chloride.

13. The process according to claim 11, wherein the reaction is performed in a solvent.

14. The process according to claim 13, wherein the solvent is ethyl acetate, dichloromethane, tetrahydrofuran, acetone, toluene, 1,4-dioxane and N,N-dimethylformamide, alone or in any combination.

15. A method for the treatment of myocardial infarction and cerebrovascular ischemia in a patient, comprising administering to the patient a therapeutically effective amount of the compound according to claim 1.

16. The method according to claim 15, wherein the compound is a compound of the formula (II):

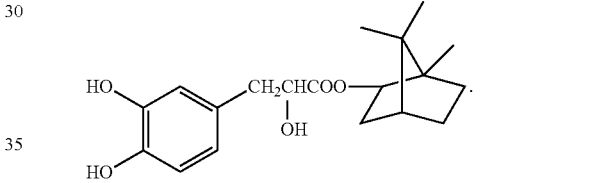

(II)

* * * * *